United States Patent
Selness et al.

(10) Patent No.: US 9,359,300 B2
(45) Date of Patent: *Jun. 7, 2016

(54) METHYL/DIFLUOROPHENYL-METHOXY SUBSTITUTED PYRIDINONE-PYRIDINYL COMPOUNDS, METHYL-PYRIDINYL-METHOXY SUBSTITUTED PYRIDINONE-PYRIDINYL COMPOUNDS, AND METHYL-PYRIMIDINYL-METHOXY SUBSTITUTED PYRIDINONE-PYRIDINYL COMPOUNDS

(71) Applicant: CONFLUENCE LIFE SCIENCES INC., St. Louis, MO (US)

(72) Inventors: Shaun R. Selness, Chesterfield, MO (US); Joseph B. Monahan, St. Louis, MO (US); John F. Schindler, Chesterfield, MO (US); Balekudru Devadas, Chesterfield, MO (US); Susan L. Hockerman, Kirkwood, MO (US)

(73) Assignee: CONFLUENCE LIFE SCIENCES, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/913,350

(22) Filed: Jun. 7, 2013

(65) Prior Publication Data

US 2013/0274272 A1 Oct. 17, 2013

Related U.S. Application Data

(63) Continuation-in-part of application No. 13/312,924, filed on Dec. 6, 2011, now abandoned.

(60) Provisional application No. 61/420,074, filed on Dec. 6, 2010.

(51) Int. Cl.
| | |
|---|---|
| *C07D 401/14* | (2006.01) |
| *A61K 31/4412* | (2006.01) |
| *C07D 213/69* | (2006.01) |
| *A61K 31/506* | (2006.01) |
| *A61K 45/06* | (2006.01) |
| *A61K 31/444* | (2006.01) |

(52) U.S. Cl.
CPC ............ *C07D 213/69* (2013.01); *A61K 31/444* (2013.01); *A61K 31/4412* (2013.01); *A61K 31/506* (2013.01); *A61K 45/06* (2013.01); *C07D 401/14* (2013.01)

(58) Field of Classification Search
CPC .............. C07D 401/14; A61K 31/4412
USPC ........... 544/296, 333; 546/257; 514/256, 332, 514/334
See application file for complete search history.

(56) References Cited

U.S. PATENT DOCUMENTS

| 7,067,540 | B2 | 6/2006 | Devadas et al. ............... 514/348 |
| 7,345,054 | B2 | 3/2008 | Hale et al. ...................... 514/300 |
| 2005/0176775 | A1 | 8/2005 | Devadas et al. ............... 514/340 |
| 2007/0003993 | A1 | 1/2007 | Kritzman et al. ............... 435/12 |
| 2007/0167621 | A1 | 7/2007 | Durley ............................ 544/60 |
| 2009/0030017 | A1 | 1/2009 | Hanada et al. ................ 514/256 |

FOREIGN PATENT DOCUMENTS

| CN | 1646125 | 7/2005 | ......... A61K 31/4412 |
| EP | 1447401 | 8/2004 | ........... C07D 211/76 |
| EP | 1741702 | 1/2007 | ........... C07D 211/82 |
| JP | 2005-255675 | 9/2005 | ......... A61K 31/4418 |

(Continued)

OTHER PUBLICATIONS

Boehm et al., New Inhibitors of p38 kinase, Expert Opinion in Therapeutic Patents, 10(1), pp. 25-37, (2000).*
Dodeller et al., The p38 mitogen-activated protein kinase signalling cascade in CD4 T cells, Arthritis Research & Therapy, vol. 8, No. 2, (2006). Online at http://arthritis-research.com/content/8/2/205.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak Rao
(74) *Attorney, Agent, or Firm* — Harness, Dickey & Pierce, P.L.C.

(57) ABSTRACT

The present disclosure provides methyl/difluorophenyl-methoxy substituted pyridinone-pyridinyl compounds, methyl-pyridinyl-methoxy substituted pyridinone-pyridinyl compounds, and methyl-pyrimidinyl-methoxy substituted pyridinone-pyridinyl compounds useful in the treatment of p38 kinase mediated diseases, such as lymphoma and auto-inflammatory disease, having the structure of Formula (I):

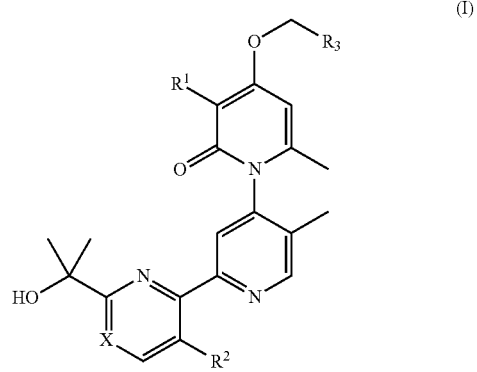

wherein $R^1$, $R^2$, $R^3$ and X are as defined in the detailed description; pharmaceutical compositions comprising at least one of the compounds; and methods for treating p38 kinase mediated diseases using the compound.

13 Claims, No Drawings

(56) References Cited

FOREIGN PATENT DOCUMENTS

| WO | WO 00/17175 | 3/2000 | ............ C07D 277/48 |
|---|---|---|---|
| WO | WO 00/71535 | 11/2000 | ............ C07D 401/06 |
| WO | WO 02/42292 | 5/2002 | ............ C07D 401/06 |
| WO | WO 03/068230 | 8/2003 | ......... A61K 31/4412 |
| WO | WO 2004/014859 | 2/2004 | ............ C07D 213/00 |
| WO | WO 2004/024078 | 3/2004 | |
| WO | WO 2004/087677 | 10/2004 | ............ C07D 239/00 |
| WO | WO 2005/018557 | 3/2005 | |
| WO | WO 2005/077050 | 8/2005 | |
| WO | WO 2006/109876 | 10/2006 | ............ A61K 31/444 |
| WO | WO 2007/006591 | 1/2007 | ............ C07D 213/64 |
| WO | WO 2007/141200 | 12/2007 | ............ C07D 213/69 |
| WO | WO 2008/062905 | 5/2008 | ............ C07D 413/10 |
| WO | WO 2008/073306 | 6/2008 | ............ C07D 213/75 |
| WO | WO 2007/081901 | 7/2008 | ............ A61K 31/513 |
| WO | WO 2008/153942 | 12/2008 | ............ A01N 43/54 |
| WO | WO 2009/012275 | 1/2009 | ............ C07D 401/12 |
| WO | WO 2009/012277 | 1/2009 | ............ C07D 401/12 |
| WO | WO 2009/156484 | 12/2009 | ............ C07D 213/81 |
| WO | WO 2011/003007 | 1/2011 | ............. A61K 31/50 |
| WO | WO 2011/003012 | 1/2011 | ............. A61K 31/50 |
| WO | WO 2011/003021 | 1/2011 | ............. A61K 31/50 |

OTHER PUBLICATIONS

Simone, Oncology: Introduction, Cecil Textbook of Medicine, 20th Edition, vol. 1, pp. 1004-1010, 1996.*

Davidson, W. et al., (2004) "Discovery and characterization of a substrate selective p38alpha inhibitor" Biochemistry 43: 11658-71.

Burnette, BL. et al., (2009) "SD0006: a potent, selective and orally available inhibitor of p38 kinase" *Pharmacology* 84(1): 42-60.

Deady, L. et al., (1998) "Studies on the synthesis of benzimidazo[2,1-a]isoquinolines" *Austrailian Journal of Chemistry* 51(10): 941-45.

Kato, T. et al., (1964) "Ketene and its derivatives. VIII. Reactions of diketene with amino heterocycles." *Yakugaku Zasshi* 34(12): 1201-5.

Kato, T. et al., (1964) "Studies on Ketene and its Derivatives. VI. Reaction of diketene with aminopyridines and their N-oxides." *Chem. Pharm. Bull.* 12(8): 910-16.

Kato, T. et al., (1972) "Studies on Ketene and Its Derivatives. XLVI. Mass spectrometric studies of 3-Acetyl-4-hydroxy-6-methyl-I-pyridyl-2-pyridones and N-Pyridyl-2, 6-dimethyl-4-pyrone-3-carboxamides." *Chem. Pharm. Bull.* 20(1): 133-41.

Sherlock, M. et al., (1988) "Antiallergy agents. 1. Substituted 1,8-naphthyridin-2(1H)-ones as inhibitors of SRS-A release." *J. Med. Chem.* 31(11): 2108-21.

Tonkiha, N. et al., (2005) "Syntheses of 7,8-dihydro-9H-pyrido[3,2-b][1,4]diazepin-8-ones and 2,3-dihydro-1H-1,5-benzodiazepines in reactions of 4-hydroxycoumarin and 4-hydroxy-6-methyl-2H-pyran-2-one with aromatic o-diamines." *Latvijas Kimijas Zurnals* 1: 51-60.

Hu, E., et al. (2008) "Discovery of Aryl Aminoquinazoline Pyridones as Potent, Selective, and Orally Efficacious Inhibitors of Receptor Tyrosine Kinase e-Kit.", *J. Med. Chem.*, 51(11):3065-3068.

Chinese Office Action dated Jun. 6, 2014 in Chinese Application No. 201180066860.X with English translation.

Supplementary European Search Report in European Application No. 11847595.3 dated Mar. 25, 2014.

\* cited by examiner

METHYL/DIFLUOROPHENYL-METHOXY SUBSTITUTED PYRIDINONE-PYRIDINYL COMPOUNDS, METHYL-PYRIDINYL-METHOXY SUBSTITUTED PYRIDINONE-PYRIDINYL COMPOUNDS, AND METHYL-PYRIMIDINYL-METHOXY SUBSTITUTED PYRIDINONE-PYRIDINYL COMPOUNDS

CROSS-REFERENCE TO RELATED APPLICATIONS

This application is a Continuation-in-Part of U.S. application Ser. No. 13/312,924 filed 6 Dec. 2011, and published as U.S. Patent Publication 2012/0142709 on 7 Jun. 2012 which claims the benefit of U.S. Provisional Application No. 61/420,074, filed on 6 Dec. 2010. The entire disclosure of each of the above applications is incorporated herein by reference.

FIELD

The present disclosure generally relates to a compound having enzyme inhibitory activity, pharmaceutical compositions comprising the compound, and methods useful for treating diseases. More specifically, the present disclosure relates to a class of pyrimidinone-phenyl-pyrimindinyl compounds, pharmaceutical compositions comprising the compound, and methods useful for treating p38 kinase mediated diseases.

BACKGROUND

Mitogen-activated protein kinases (MAPK) are a conserved family of enzymes that relay and propagate external stimuli, using phosphorylation cascades to generate a coordinated cellular response to the environment. The MAPK are proline-directed serine/threonine-specific protein kinases that regulate cellular activities, such as gene expression, mitosis, differentiation, and cell survival/apoptosis. To date, four distinct classes of mammalian MAPK have been identified: the extracellular signaling kinases (ERK1 and 2), the c-jun N-terminal kinase-1 (JNK1-3), the p38 MAPK (p38α, β, γ, and δ), and ERK5. The MAPK are activated by the dual phosphorylation of Thr and Tyr residues within a TXY activation motif by coordinated dual-specificity MAPKK, where X is Glu, Pro, and Gly in ERK, JNK, and p38 MAPK, respectively. MAPK are 60-70% identical to each other, yet differ in their activation loop sequences and sizes. The activation loop is adjacent to the enzyme-active site, and its phosphorylation allows the enzyme to reposition active-site residues into the optimal orientation for substrate binding and catalysis. Downstream substrates of MAPK include mitogen-activated protein-kinase-activated protein (MAPKAP) kinases and transcription factors, the phosphorylation of which, either directly or indirectly, regulates gene expression at several points, including transcription, nuclear export, and mRNA stability and translation. The cellular consequences of MAPK activation include inflammation, apoptosis, differentiation, and proliferation.

Distinct genes encode four p38 MAPKinases in humans: p38α, β, γ, and δ. Significant amino acid sequence homology is observed among the 4 isoforms, with 60%-75% overall sequence identity and >90% identity within the kinase domains. Tissue-selective expression is observed, with p38γ found predominantly in skeletal muscle, p38δ in the testes, pancreas, and small intestine. In contrast, p38α and β are more ubiquitously expressed.

An understanding of the broad biologic and pathophysiological roles of p38 MAPK family members has grown significantly over the past decade, as has the complexity of the signaling network leading to their activation. Scientific exploration of this pathway from biological, cellular, and in vivo perspectives was largely enabled by the availability of well-behaved, selective, small-molecule inhibitors of p38 MAPK that target the α and, to a lesser extent, β isoforms. p38α MAPK is the major isoform involved in the immune and inflammatory response. As such its function is critical for the production and activity of multiple pro-inflammatory cytokines, including TNFα, IL-1, IL-6, and IL-8, in cells such as macrophages, monocytes, synovial cells, and endothelial cells. p38 MAPK is also responsible for the induction of key inflammatory enzymes such as COX2 and iNOS, the major sources of eicosanoids and nitric oxide at sites of inflammation, respectively. Additionally, the p38 MAPK pathway regulates the expression of matrix metalloproteinases (MMP), including MMP2, MMP9, and MMP13.

The use of selective and potent inhibitors has facilitated the discovery of several families of p38 MAPK substrates, including transcription factors, MAPKAP kinases, and other enzymes. p38 MAPK can directly phosphorylate several transcription factors, such as myocyte-specific enhancer binding factor 2C (MEF2C), CHOP, peroxisome proliferator-activated receptor (PPAR) α, PPAR γ co-activator 1 and p53. These transcription factors are involved in cellular functions such as apoptosis, gluconeogenesis, and synthesis of enzymes involved in fatty acid oxidation. p38 MAPK is also involved in the direct or indirect phosphorylation of enzyme substrates, such as cytosolic phospholipase A2, and the Cdc25 phosphatases, which are involved in the activation of cyclin-dependent protein kinase activity and cell-cycle regulation. Therefore in addition to its role in the inflammatory response, p38 MAPK has other functions associated with normal and abnormal cell growth and survival as well as cellular function and homeostasis.

The MAPKAP kinases—MK2, MK-3, and PRAK—are selectively phosphorylated by p38 MAPK, while the phosphorylation of MSK1/2, MNK1/2, and RSKb is catalyzed by both p38 MAPK and ERK. Activation of RSKb is thought to play a role in cell survival, although the identification of substrates has been difficult, due to the lack of specific inhibitors. MNK is involved in the phosphorylation of eukaryotic initiation factor-4E, which binds to the 'cap' structure of mRNA and enhances protein translation. MNK phosphorylates the mRNA binding protein hnRNP-A0, a protein that regulates mRNA stability of transcripts encoding inflammatory proteins. MSK1/2 is involved in the phosphorylation of the transcription factors CREB and ATF-1, which regulate AP-1 binding proteins. In addition, MSK1/2 can phosphorylate Histone H3, which is involved in chromatin remodeling. While evidence suggests that MSK and MNK play a role in the mediation of pro-inflammatory cytokines, in vivo data with selective inhibitors and/or knockout mice are lacking.

MK-2, MK-3, and PRAK, once phosphorylated and activated by p38 MAPK, share similar substrate specificities. All of these kinases can phosphorylate the small heat-shock protein Hsp27. Studies have shown that the PRAK- and MK3-deficient mice do not display any resistance to endotoxic shock or a decrease in lipopolysaccharide-(LPS)-induced cytokine production. In contrast, MK-2-deficient mice show a resistance to endotoxic shock and an impaired inflammatory response, as well as a significantly decreased production of cytokines such as TNFα, IFNγ and IL-6. Thus, the p38/MK2 axis specifically is necessary and sufficient for mediating pro-inflammatory responses.

Recently, Davidson et al (2004) Discovery and characterization of a substrate selective p38alpha inhibitor, *Biochemistry* 43:11658-71, described a novel approach for increasing selectivity of a p38 MAPK inhibitors. In these studies, a high throughput screen was carried out using an assay that measured the p38-dependent phosphorylation and activation of MK2. The p38:MK2 complex is very stable with a Kd of 6 nM. The binding affinity of p38 for MK2 is driven by the C-terminal domain of MK2 containing several positively charged amino acid residues. Crystallographic studies of the p38:MK2 complex demonstrated that the C-terminal region of MK2 wraps around p38α and binds to the negatively charged ED binding site. The tight binding of p38 to MK2 may give rise to conformational changes providing additional binding pockets for inhibitors that would specifically be dependent upon the p38:MK2 interaction.

Taking advantage of the p38:MK2 interaction and using MK2 as the p38 substrate, a novel inhibitor of p38α was discovered exhibiting interesting properties (Davidson et al). This inhibitor demonstrated substrate selectivity by preventing the p38α dependent phosphorylation of MK2 (Ki app 300 nM) while sparing the p38α dependent phosphorylation of ATF2 (Ki app>20 uM). This novel inhibitor is functionally unique compared with traditional p38 ATP competitive inhibitors that block the p38-dependent phosphorylation of all p38 substrates. A second independent study also describes p38 inhibitors with unique mechanistic properties. This work demonstrates a novel mechanism for the selective inhibition of the p38 dependent phosphorylation of MK2. Unlike the previous study of Davidson et al., these mechanistically unique compounds are competitive with ATP and stabilize the p38/MK2 complex. Taken together, these two studies clearly prove the concept that selective p38/MK2 axis blockade is achievable with small molecule inhibitors. In comparison to traditional p38 MAPK inhibitors these p38/MK2 inhibitors should retain or enhance potency and exhibit improved safety features in animal models of disease or in human clinical settings.

The p38/MK2 role in the regulation of inflammatory cytokines (TNFα, IL-1β, IL-6) and enzymes responsible for inflammation (COX-2, iNOS, and MMPs) makes it an attractive drug target. Several classical p38 MAPK inhibitors have progressed to testing in clinical trials. Some of these candidates have failed, for safety or other reasons, but several have reported clinical data in diseases such as rheumatoid arthritis, pain, Crohn's disease, acute coronary syndrome, multiple myeloma and chronic obstructive pulmonary disease. In addition to these diseases several IL-1β mediated diseases could be impacted by a p38 inhibitor based upon the key role for the p38 MAPK pathway in the biosynthesis and activity of this cytokine. These diseases include the family of cryopyrin associated periodic disorders (CAPS), chronic gout, diabetes, Still's disease, Familial Mediterranean Fever among others.

In addition to human inflammatory pathways, p38 MAPK has been linked to canine B cell growth and survival. The role of p38 MAPK in B cell growth suggests that inhibition of this enzyme may be therapeutically beneficial for the treatment of canine B cell lymphoma. Canine lymphoma is one of the most common malignancies diagnosed in companion animals representing 10-25% of canine neoplasms and >80% of the hematopoietic tumors. An orally available, selective B cell growth inhibitor would meet a significant unmet medical need.

Compounds useful for treating diseases and conditions caused or exacerbated by unregulated p38 MAP Kinase and/or TNF activity are described in WO 2000/017175 published 30 Mar. 2000. The compounds described therein include a class of substituted urea compounds.

Compounds useful for treating diseases and conditions caused or exacerbated by unregulated p38 MAP Kinase and/or TNF activity are described in WO 2000/071535 published 30 Nov. 2000. The compounds described therein include a class of indole-type compounds.

Compounds useful for treating diseases and conditions caused or exacerbated by unregulated p38 MAP Kinase and/or TNF activity are described in WO 2002/042292 published 30 May 2002. The compounds described therein include a class of coupled indole-type derivatives.

Compounds useful for prophylaxis or treatment of circulatory diseases, metabolic diseases and/or central nervous system diseases are described in WO 2008/062905 published 29 May 2008. The compounds described therein include an alkyl-pyrimidinone-phenyl compounds wherein the phenyl fragment is substituted with a cyclopropyl radical, e.g., 6-butyl-3-(3-cyclopropylphenyl)-2-methyl-5-{[2'-(5-oxo-4,5-dihydro-1,2,4-oxadizol-3-yl)biphenyl-4-yl]methyl}pyrimidin-4(3H)-one.

Various potential inhibitors or modulators of p38 kinase and the p38 kinase pathway are described in WO 2005/018557 published 3 Mar. 2005. The compounds described therein include di-fluorophenyl-methoxy-pyridinone-pyridyl compounds wherein the pyridyl fragment is substituted with various radicals including alkyl, alkenyl, hydroxyalkyl, halo, cyano, amino, carboxy, carbamoyl, methoxycarbonyl and hydroxyalkenylimino radicals.

Compounds useful for treating diseases and conditions caused or exacerbated by unregulated p38 MAP Kinase and/or TNF activity are described in US 2007/0167621 published 19 Jul. 2007. The compounds described therein include di-fluorophenyl-methoxy-pyrimidinone-phenyl compounds wherein the phenyl fragment is substituted with methyl amido radical.

Compounds useful for treating diseases and conditions caused or exacerbated by unregulated p38 MAP Kinase and/or TNF activity are described in WO 2004/087677 published 14 Oct. 2004. The compounds described therein include di-fluorophenyl-methoxy-pyrimidinone-phenyl compounds wherein the phenyl fragment is substituted with piperazinyl or a morpholinyl radical through a carbonyl bridge.

Pyrimidinone derivatives (as inhibitors of protein kinases and useful in treating disorders related to abnormal protein kinase activities such as inflammatory diseases and certain types of cancer), are described in WO 2007/081901 published 19 Jul. 2008. The compounds described therein include di-fluorophenyl-methoxy-pyrimidinone-phenyl compounds wherein the phenyl fragment is substituted with a cyclopropanyl or a morpholinyl radical through an amidoalkylamido bridge.

Pyrimidinone derivatives (as inhibitors of protein kinases and useful in treating disorders related to abnormal protein kinase activities such as inflammatory diseases and certain types of cancer) are described in WO 2008/153942 published 18 Dec. 2008. The compounds described therein include di-fluorophenyl-methoxy-pyrimidinone-phenyl compounds where the phenyl radical is substituted with cyclopentyl or a cyclohexyl radical through an amido bridge.

Compounds useful for treating diseases and conditions caused or exacerbated by unregulated p38 MAP Kinase and/or TNF activity are described in U.S. Pat. No. 7,067,540 published 27 Jun. 2007. The compounds described therein include di-fluorophenyl-methoxy-pyridinone-phenyl compounds wherein the phenyl radical is substituted with a five-membered heteroaryl radical (e.g., pyrazolyl or imidazolyl).

SUMMARY

In one embodiment, there is provided a compound of Formula (I):

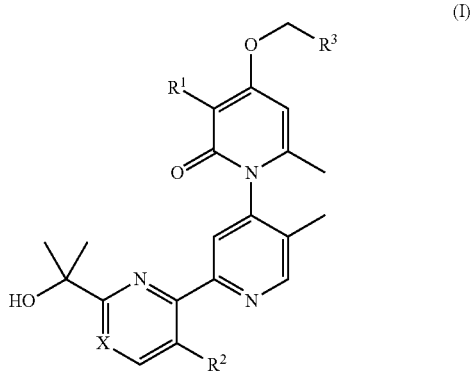

and a pharmaceutically acceptable salts thereof; wherein $R^1$, $R^2$, $R^3$, and X are as defined in the detailed description.

DETAILED DESCRIPTION

The following description is merely exemplary in nature and is not intended to limit the present disclosure, application, or uses.

A. Definitions

The use of generic terms in the description of the compounds are herein defined for clarity.

This specification uses the terms "substituent", "radical", "group", "moiety", and "fragment" interchangeably.

The term "hydrido" denotes a single —H atom (H) and may be used interchangeably with the symbol "H" or the term "hydrogen".

If a substituent is described as being "optionally substituted," the substituent may be either (1) not substituted or (2) substituted. If a substitutable position is not substituted, the default substituent is a hydrido radical.

As used herein, the singular forms "a" and "an" may include plural reference unless the context clearly dictates otherwise.

The term "alkyl", either alone or within other terms such as "haloalkyl" and "alkylaryl", refers to an acyclic alkyl radical containing 1, 2, 3, 4, 5, 6, 7, 8, 9 or 10 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

The term "alkoxy" is RO— where R is alkyl as defined herein. Non-limiting examples of alkoxy groups include methoxy, ethoxy and propoxy. The terms alkyloxy and alkoxy may be used interchangeably.

The term "aryl" refers to any monocyclic, bicyclic or tricyclic carbon ring of up to 6 atoms in each ring, wherein at least one ring is aromatic, or an aromatic ring system of 5 to 14 carbons atoms which includes a carbocyclic aromatic group fused with a 5- or 6-membered cycloalkyl group. Examples of aryl groups include, but are not limited to, phenyl, naphthyl, tetrahydronaphthyl and indanyl.

The term "arylalkyl" embraces an aryl-substituted alkyl radical and may be used interchangeably with the term "aralkyl". Examples include benzyl, diphenylmethyl, triphenylmethyl, phenylethyl and diphenylethyl. The terms benzyl and phenylmethyl are interchangeable.

The term "aryloxy" is RO—, where R is aryl. "Arylthio" is RS—, where R is aryl.

The term "heteroaryl" refers to a monocyclic, bicyclic or tricyclic ring having up to 6 atoms in each ring, wherein at least one ring is aromatic and contains from 1 to 4 heteroatoms in the ring selected from the group consisting of N, O and S, Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

The term "hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

The number of carbon atoms in a hydrocarbyl substituent can be indicated by the prefix "$C_X$—$C_Y$" where X is the minimum and Y is the maximum number of carbon atoms in the substituent.

The term "pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

The term "pharmaceutically-acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-enel-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

Compounds of the present invention can exist in tautomeric, geometric or stereoisomeric forms. The compounds' corresponding esters, metabolites, oximes, prodrugs, oniums and N-oxides are also embraced by the invention. The present invention contemplates all such compounds, including cis- and trans-geometric isomers, E- and Z-geometric isomers, R- and S-enantiomers, diastereomers, atropisomers, d-isomers, l-isomers, mixtures of isomers and racemates thereof, as falling within the scope of the invention.

The terms "cis" and "trans" denote a form of geometric isomerism in which two carbon atoms connected by a double bond will each have a radical atom on the same side of the double bond ("cis") or on opposite sides of the double bond ("trans").

Some of the compounds described contain one or more stereocenters and are meant to include R, S and mixtures of R and S forms for each stereocenter present.

The term "atropisomerism" refers to a type of isomerism resulting from hindered rotation around a single bond due to steric strain of the substituents. This phenomenon creates stereoisomers which display axial chirality.

The compounds of the invention may also exist as atropisomers, i.e., chiral rotational isomers. The invention encompasses racemates, resolved atropisomers, and mixtures thereof.

Atropisomers are generally stable but can often be equilibrated thermally. Atropisomers will have the same but opposite optical rotation. Like chiral compounds each atropisomers may have different properties when bound to an enzyme or receptor with one isomer often being more potent than the other. Atropisomers are frequently used as pharmaceutical agents.

The term "2,4-difluoro-3-methylphenyl" refers to a moiety having structure:

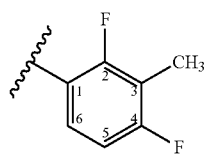 [SMILES: *c1ccc(F)c(C)c1F]

The term "2,4-difluoro-5-methylphenyl" refers to a moiety having structure:

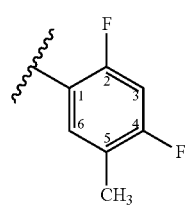 [SMILES: *c1cc(C)c(F)cc1F]

The term "5-methylpyridin-3-yl" refers to a moiety having structure:

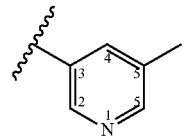 [SMILES: *c1cncc(C)c1]

The term "4-methylpyrimidin-2-yl" refers to a moiety having structure:

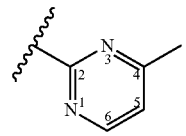 [SMILES: *c1nccc(C)n1]

List of Abbreviations:
ACN acetonitrile
Boc tert-butyloxycarbonyl
Bu butyl
Bpy 2,2'-bipyridine
DCA dichloroacetic acid
DCI dicyclohexylcarbodiimide
DCM dichloromethane or methylenechloride
DIPEA diisopropylethylamine
DMA dimethylacetamide
DMAP 4-dimethylaminopyridine or N,N-dimethylaminopyridine
DME 1,2-dimethoxyethane
DMF N,N-dimethylformamide
DMSO dimethylsulfoxide
$CuBr_2$ copper(II)bromide
EDAC N-(3-dimethylaminopropyl)-N'-ethylcarbodiimide hydrochloride
eq. equivalents
Et ethyl
EtOAC ethyl acetate
EtOH ethanol
HPLC high pressure liquid chromatography
h hour(s)
IPA isopropyl alcohol
$K_2CO_3$ potassium carbonate
KOtBu potassium tert-butoxide
LAH lithium aluminum hydride
LC/MS liquid chromatography mass spectrometry
LC/MS/MS liquid chromatography tandem mass spectrometry
mCPBA m-chloroperbenzoic acid
Me methyl
MeCN acetonitrile
MeOH methanol
$MgSO_4$ magnesium sulfate
mL milliliter
mmol millimole
NaH sodium hydride
$NaN(TMS)_2$ sodium bis(trimethylsilyl)amide
NCS n-chloro succinimide
NMR nuclear magnetic resonance
Pd/C palladium on carbon
Ph phenyl
PPA polyphosphoric acid
TEA triethylamine TFA trifluoroacetic acid
THF tetrahydrofuran
TOSMIC toluenesulfonylmethyl isocyanide
TSA p-toluenesulfonic acid.

B. Compounds

The present disclosure provides a compound having the structure of Formula (I):

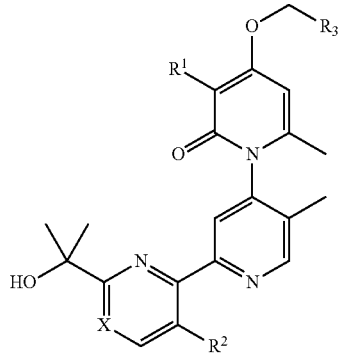

(I)

and a pharmaceutically acceptable salt thereof, wherein:
X is CH or N;
$R^1$ is chloro or bromo;
$R^2$ is —H or methyl; and $R^3$ is selected from the group consisting of 2,4-difluoro-3-methylphenyl, 2,4-difluoro-5-methylphenyl, 5-methylpyridin-3-yl, and 4-methylpyrimidin-2-yl.

The present disclosure provides a compound having the structure of Formula (II):

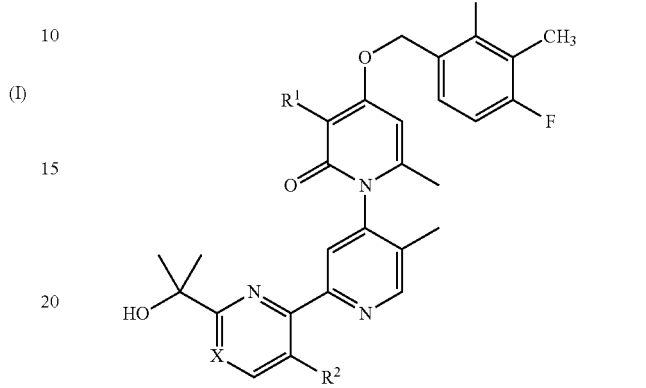

(II)

and a pharmaceutically acceptable salt thereof, wherein:
X is CH or N;
$R^1$ is chloro or bromo; and
$R^2$ is —H or methyl.

Non-limiting examples of Formula (II) compounds include the following compounds and pharmaceutically acceptable salts thereof:

| No. | Structure | Compound Name |
|---|---|---|
| 1 | ![structure] | 3-chloro-4-((2,4-difluoro-3-methylbenzyl)oxy)-2'-(2-(2-hydroxypropan-2-yl)pyrimidin-4-yl)-5',6-dimethyl-2H-[1,4'-bipyridin]-2-one |
| 2 | ![structure] | 3-bromo-4-((2,4-difluoro-3-methylbenzyl)oxy)-2'-(2-(2-hydroxypropan-2-yl)pyrimidin-4-yl)-5',6-dimethyl-2H-[1,4'-bipyridin]-2-one |

-continued

| No. | Structure | Compound Name |
|---|---|---|
| 3 | 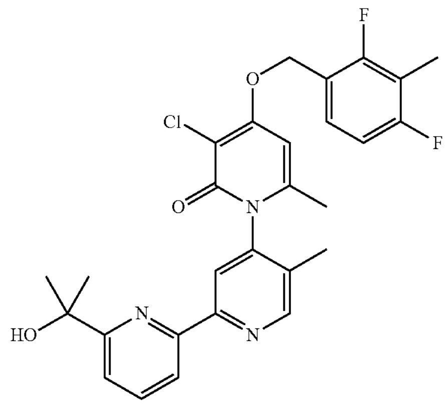 | 3-chloro-4-((2,4-difluoro-3-methylbenzyl)oxy)-6''-(2-hydroxypropan-2-yl)-5',6-dimethyl-2H-[1,4':2',2''-terpyridin]-2-one |
| 4 | 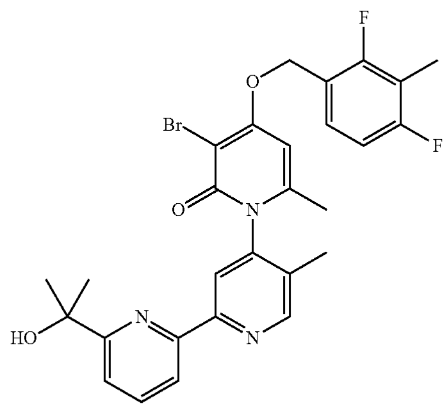 | 3-bromo-4-((2,4-difluoro-3-methylbenzyl)oxy)-6''-(2-hydroxypropan-2-yl)-5',6-dimethyl-2H-[1,4':2',2''-terpyridin]-2-one |
| 5 | 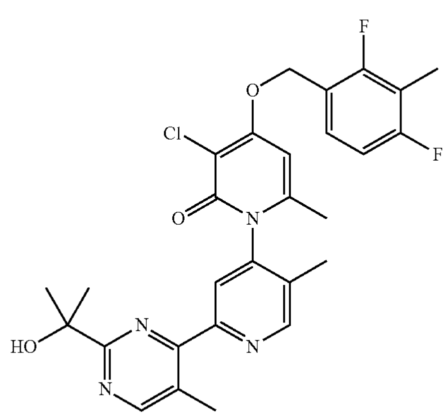 [SMILES: Cc1cnc(-c2nc(C(C)(C)O)ncc2C)cc1-n1c(C)cc(OCc2ccc(F)c(C)c2F)c(Cl)c1=O] | 3-chloro-4-((2,4-difluoro-3-methylbenzyl)oxy)-2'-(2-(2-hydroxypropan-2-yl)-5-methylpyrimidin-4-yl)-5',6-dimethyl-2H-[1,4'-bipyridin]-2-one |

| No. | Structure | Compound Name |
|---|---|---|
| 6 | 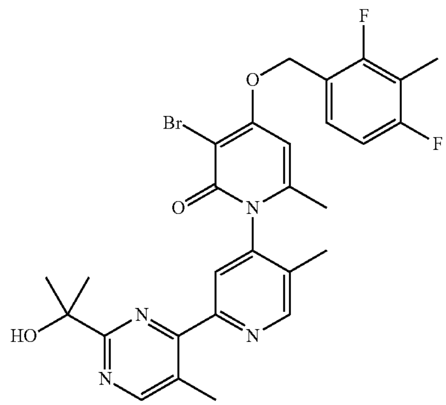 [SMILES: Cc1cnc(-c2nc(C(C)(C)O)ncc2C)cc1-n1c(C)cc(OCc2ccc(F)c(C)c2F)c(Br)c1=O] | 3-bromo-4-((2,4-difluoro-3-methylbenzyl)oxy)-2'-(2-(2-hydroxypropan-2-yl)-5-methylpyrimidin-4-yl)-5',6-dimethyl-2H-[1,4'-bipyridin]-2-one |
| 7 | 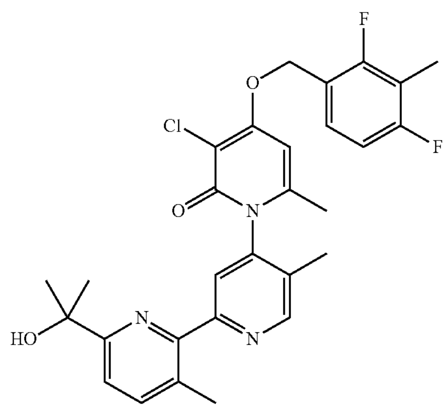 [SMILES: Cc1cnc(-c2nc(C(C)(C)O)ccc2C)cc1-n1c(C)cc(OCc2ccc(F)c(C)c2F)c(Cl)c1=O] | 3-chloro-4-((2,4-difluoro-3-methylbenzyl)oxy)-6''-(2-hydroxypropan-2-yl)-3'',5',6-trimethyl-2H-[1,4':2',2''-terpyridin]-2-one |
| 8 | 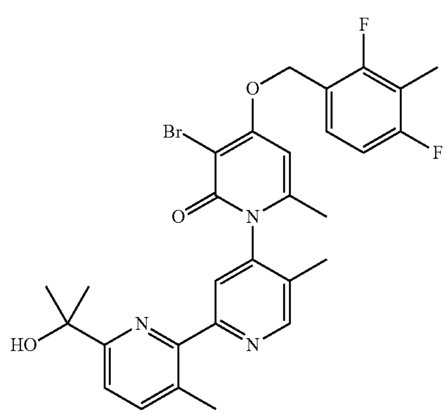 [SMILES: Cc1cnc(-c2nc(C(C)(C)O)ccc2C)cc1-n1c(C)cc(OCc2ccc(F)c(C)c2F)c(Br)c1=O] | 3-bromo-4-((2,4-difluoro-3-methylbenzyl)oxy)-6''-(2-hydroxypropan-2-yl)-3'',5',6-trimethyl-2H-[1,4':2',2''-terpyridin]-2-one |

In another embodiment, there is provided a compound having the structure of Formula (III):

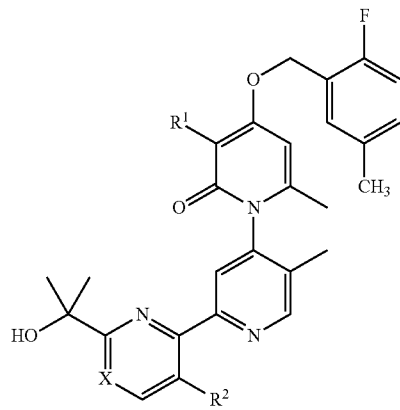

(III)

and a pharmaceutically acceptable salt thereof, wherein:

X is CH or N;

R¹ is chloro or bromo; and

R² is —H or methyl.

Non-limiting examples of Formula (III) compounds include the following compounds and pharmaceutically acceptable salts thereof:

| No. | Structure | Compound Name |
|---|---|---|
| 9 | 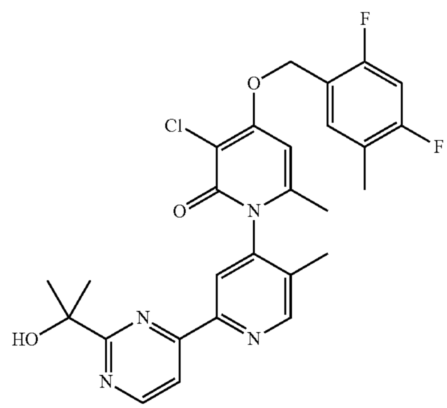 [SMILES: Cc1cc(COc2cc(C)n(-c3cc(-c4ccnc(C(C)(C)O)n4)ncc3C)c(=O)c2Cl)c(F)cc1F] | 3-chloro-4-((2,4-difluoro-5-methylbenzyl)oxy)-2'-(2-(2-hydroxypropan-2-yl)pyrimidin-4-yl)-5',6-dimethyl-2H-[1,4'-bipyridin]-2-one |
| 10 | 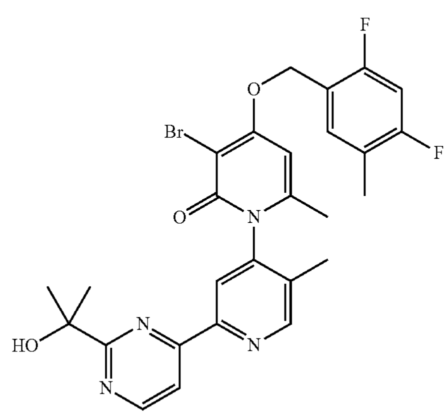 [SMILES: Cc1cc(COc2cc(C)n(-c3cc(-c4ccnc(C(C)(C)O)n4)ncc3C)c(=O)c2Br)c(F)cc1F] | 3-bromo-4-((2,4-difluoro-5-methylbenzyl)oxy)-2'-(2-(2-hydroxypropan-2-yl)pyrimidin-4-yl)-5',6-dimethyl-2H-[1,4'-bipyridin]-2-one |

| No. | Structure | Compound Name |
|---|---|---|
| 11 | 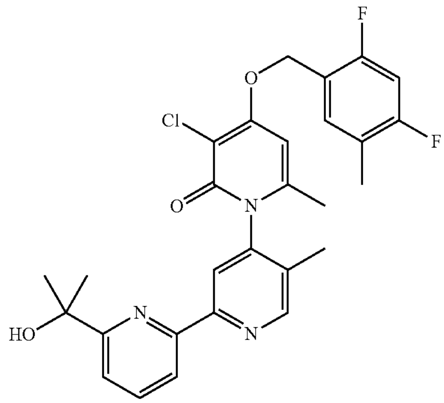 [SMILES: Cc1cc(COc2cc(C)n(-c3cc(-c4cccc(C(C)(C)O)n4)ncc3C)c(=O)c2Cl)c(F)cc1F] | 3-chloro-4-((2,4-difluoro-5-methylbenzyl)oxy)-6''-(2-hydroxypropan-2-yl)-5',6-dimethyl-2H-[1,4':2',2''-terpyridin]-2-one |
| 12 | 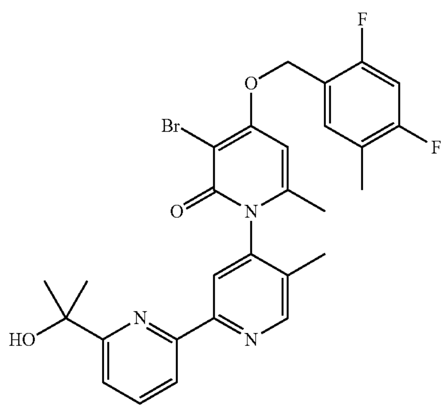 [SMILES: Cc1cc(COc2cc(C)n(-c3cc(-c4cccc(C(C)(C)O)n4)ncc3C)c(=O)c2Br)c(F)cc1F] | 3-bromo-4-((2,4-difluoro-5-methylbenzyl)oxy)-6''-(2-hydroxypropan-2-yl)-5',6-dimethyl-2H-[1,4':2',2''-terpyridin]-2-one |
| 13 | 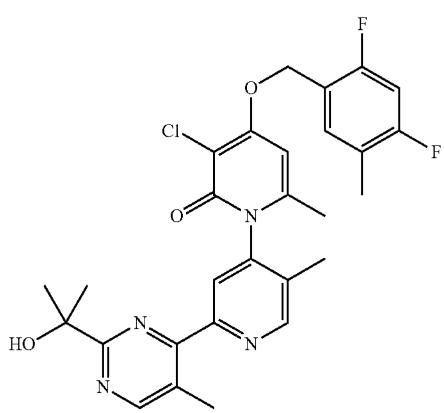 [SMILES: Cc1cc(COc2cc(C)n(-c3cc(-c4nc(C(C)(C)O)ncc4C)ncc3C)c(=O)c2Cl)c(F)cc1F] | 3-chloro-4-((2,4-difluoro-5-methylbenzyl)oxy)-2'-(2-(2-hydroxypropan-2-yl)-5-methylpyrimidin-4-yl)-5',6-dimethyl-2H-[1,4'-bipyridin]-2-one |

| No. | Structure | Compound Name |
|---|---|---|
| 14 | 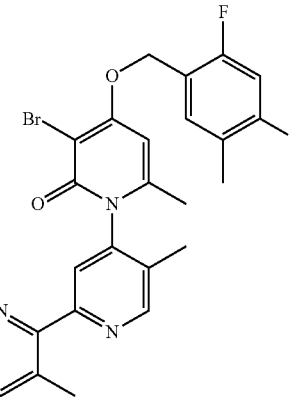 | 3-bromo-4-((2,4-difluoro-5-methylbenzyl)oxy)-2'-(2-(2-hydroxypropan-2-yl)-5-methylpyrimidin-4-yl)-5',6-dimethyl-2H-[1,4'-bipyridin]-2-one |
| 15 | 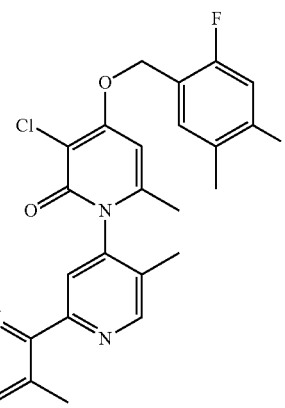 | 3-chloro-4-((2,4-difluoro-5-methylbenzyl)oxy)-6''-(2-hydroxypropan-2-yl)-3'',5',6-trimethyl-2H-[1,4':2',2''-terpyridin]-2-one |
| 16 | 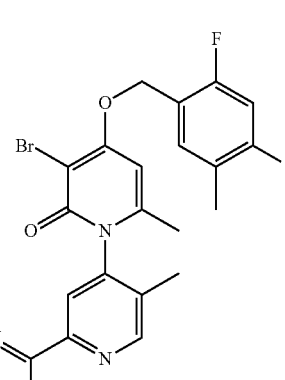 | 3-bromo-4-((2,4-difluoro-5-methylbenzyl)oxy)-6''-(2-hydroxypropan-2-yl)-3'',5',6-trimethyl-2H-[1,4':2',2''-terpyridin]-2-one |

In another embodiment, there is provided a compound having the structure of Formula (IV):

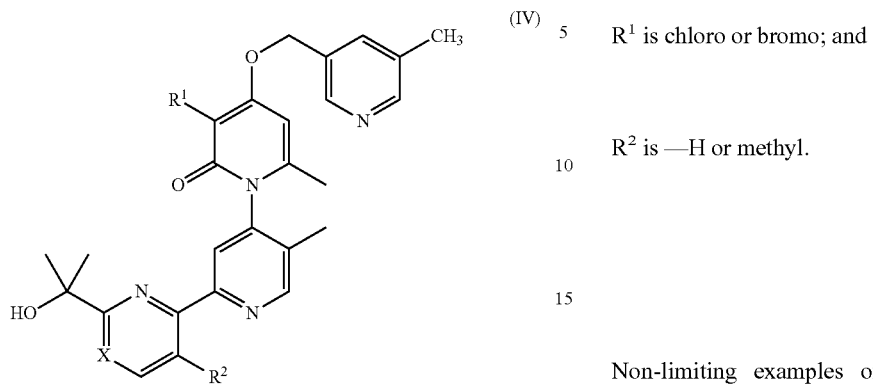

and a pharmaceutically acceptable salt thereof, wherein:

X is CH or N;

$R^1$ is chloro or bromo; and $R^2$ is —H or methyl.

Non-limiting examples of Formula (IV) compounds include the following compounds and pharmaceutically acceptable salts thereof:

| No. | Structure | Compound Name |
|---|---|---|
| 17 | 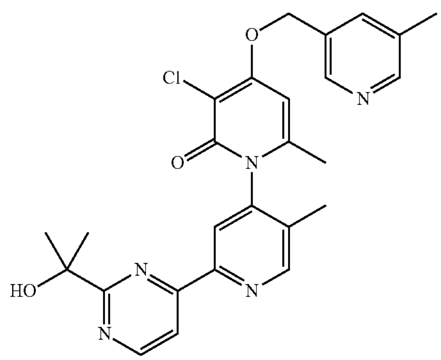 [SMILES: Cc1cncc(COc2cc(C)n(-c3cc(-c4ccnc(C(C)(C)O)n4)ncc3C)c(=O)c2Cl)c1] | 3-chloro-2'-(2-(2-hydroxypropan-2-yl)pyrimidin-4-yl)-5',6-dimethyl-4-((5-methylpyridin-3-yl)methoxy)-2H-[1,4'-bipyridin]-2-one |
| 18 | 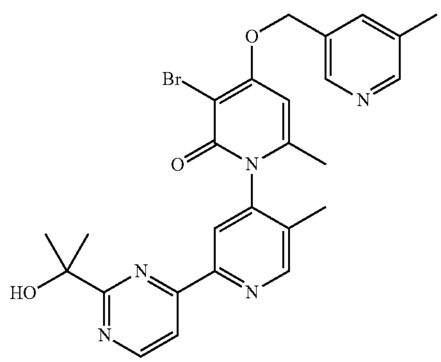 [SMILES: Cc1cncc(COc2cc(C)n(-c3cc(-c4ccnc(C(C)(C)O)n4)ncc3C)c(=O)c2Br)c1] | 3-bromo-2'-(2-(2-hydroxypropan-2-yl)pyrimidin-4-yl)-5',6-dimethyl-4-((5-methylpyridin-3-yl)methoxy)-2H-[1,4'-bipyridin]-2-one |
| 19 | 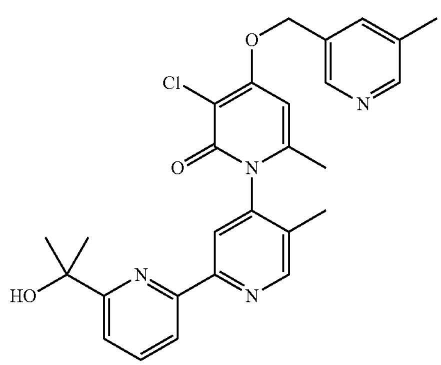 [SMILES: Cc1cncc(COc2cc(C)n(-c3cc(-c4cccc(C(C)(C)O)n4)ncc3C)c(=O)c2Cl)c1] | 3-chloro-6''-(2-hydroxypropan-2-yl)-5',6-dimethyl-4-((5-methylpyridin-3-yl)methoxy)-2H-[1,4':2',2''-terpyridin]-2-one |

-continued

| No. | Structure | Compound Name |
|---|---|---|
| 20 | 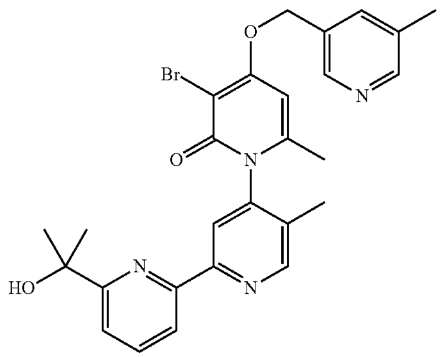 | 3-bromo-6''-(2-hydroxypropan-2-yl)-5',6-dimethyl-4-((5-methylpyridin-3-yl)methoxy)-2H-[1,4':2',2''-terpyridin]-2-one |
| 21 | 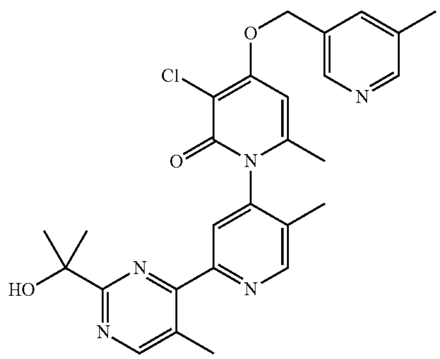 [SMILES: Cc1cncc(COc2cc(C)n(-c3cc(-c4nc(C(C)(C)O)ncc4C)ncc3C)c(=O)c2Cl)c1] | 3-chloro-2'-(2-(2-hydroxypropan-2-yl)-5-methylpyrimidin-4-yl)-5',6-dimethyl-4-((5-methylpyridin-3-yl)methoxy)-2H-[1,4'-bipyridin]-2-one |
| 22 | 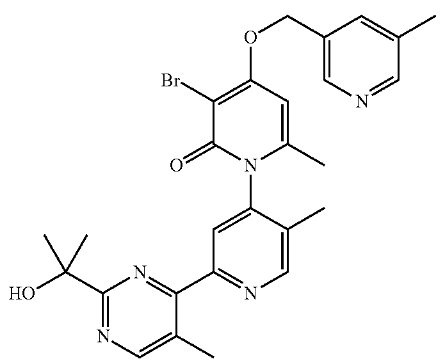 [SMILES: Cc1cncc(COc2cc(C)n(-c3cc(-c4nc(C(C)(C)O)ncc4C)ncc3C)c(=O)c2Br)c1] | 3-bromo-2'-(2-(2-hydroxypropan-2-yl)-5-methylpyrimidin-4-yl)-5',6-dimethyl-4-((5-methylpyridin-3-yl)methoxy)-2H-[1,4'-bipyridin]-2-one |
| 23 | 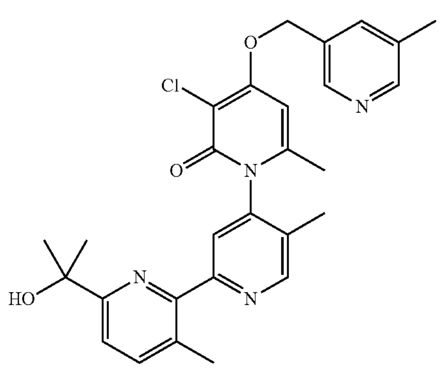 | 3-chloro-6''-(2-hydroxypropan-2-yl)-3'',5',6-trimethyl-4-((5-methylpyridin-3-yl)methoxy)-2H-[1,4':2',2''-terpyridin]-2-one |

| No. | Structure | Compound Name |
|---|---|---|
| 24 | 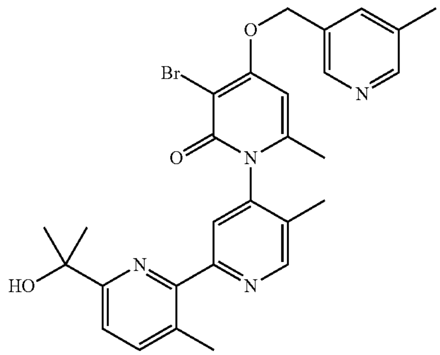 [SMILES: Cc1cncc(COc2cc(C)n(-c3cc(-c4nc(C(C)(C)O)ccc4C)ncc3C)c(=O)c2Cl)c1] | 3-bromo-6''-(2-hydroxypropan-2-yl)-3'',5',6-trimethyl-4-((5-methylpyridin-3-yl)methoxy)-2H-[1,4':2',2''-terpyridin]-2-one |

In another embodiment, there is provided a compound having the structure of Formula (V):

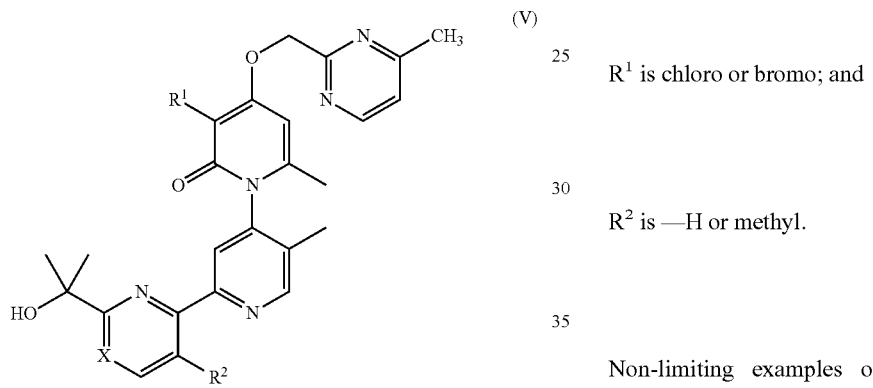

and a pharmaceutically acceptable salt thereof, wherein:

X is CH or N;

$R^1$ is chloro or bromo; and $R^2$ is —H or methyl.

Non-limiting examples of Formula (V) compounds include the following compounds and pharmaceutically acceptable salts thereof:

| No. | Structure | Compound Name |
|---|---|---|
| 25 | 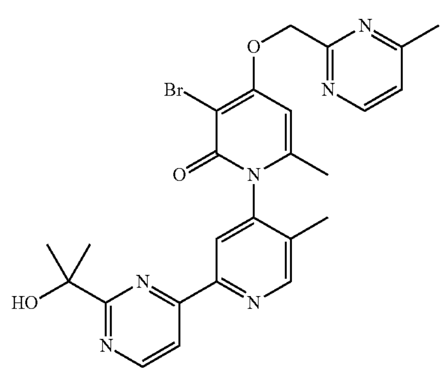 [SMILES: Cc1ccnc(COc2cc(C)n(-c3cc(-c4ccnc(C(C)(C)O)n4)ncc3C)c(=O)c2Br)n1] | 3-bromo-2'-(2-(2-hydroxypropan-2-yl)pyrimidin-4-yl)-5',6-dimethyl-4-((4-methylpyrimidin-2-yl)methoxy)-2H-[1,4'-bipyridin]-2-one |

| No. | Structure | Compound Name |
|---|---|---|
| 26 | 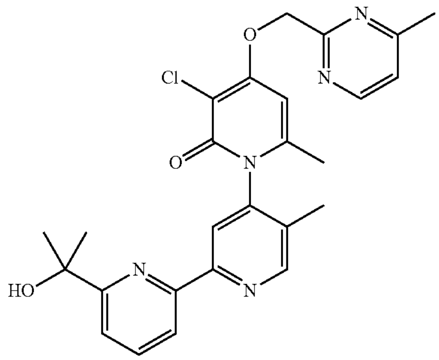 [SMILES: Cc1ccnc(COc2cc(C)n(-c3cc(-c4cccc(C(C)(C)O)n4)ncc3C)c(=O)c2Cl)n1] | 3-chloro-6''-(2-hydroxypropan-2-yl)-5',6-dimethyl-4-((4-methylpyrimidin-2-yl)methoxy)-2H-[1,4':2',2''-terpyridin]-2-one |
| 27 | 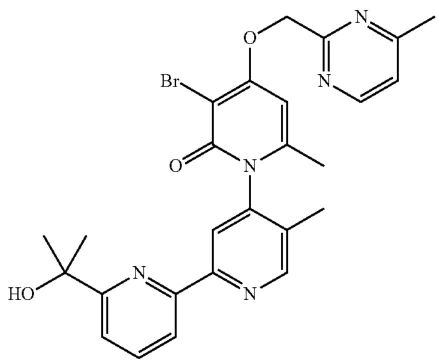 [SMILES: Cc1ccnc(COc2cc(C)n(-c3cc(-c4cccc(C(C)(C)O)n4)ncc3C)c(=O)c2Br)n1] | 3-bromo-6''-(2-hydroxypropan-2-yl)-5',6-dimethyl-4-((4-methylpyrimidin-2-yl)methoxy)-2H-[1,4':2',2''-terpyridin]-2-one |
| 28 | 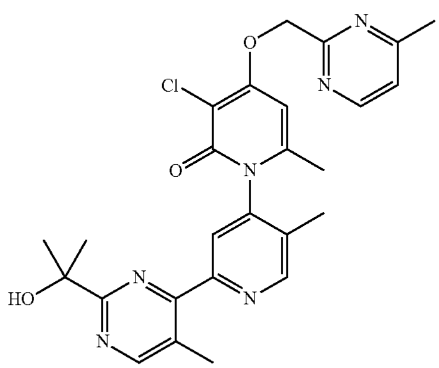 [SMILES: Cc1ccnc(COc2cc(C)n(-c3cc(-c4nc(C(C)(C)O)ncc4C)ncc3C)c(=O)c2Cl)n1] | 3-chloro-2'-(2-(2-hydroxypropan-2-yl)-5-methylpyrimidin-4-yl)-5',6-dimethyl-4-((4-methylpyrimidin-2-yl)methoxy)-2H-[1,4'-bipyridin]-2-one |
| 29 | 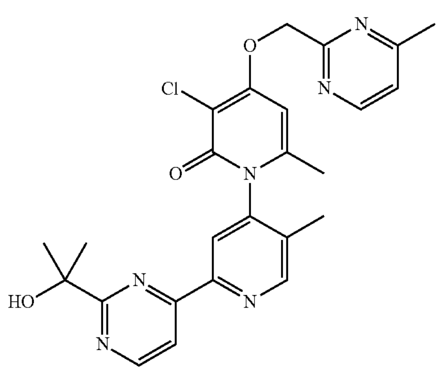 [SMILES: Cc1ccnc(COc2cc(C)n(-c3cc(-c4ccnc(C(C)(C)O)n4)ncc3C)c(=O)c2Cl)n1] | 3-chloro-2'-(2-(2-hydroxypropan-2-yl)pyrimidin-4-yl)-5',6-dimethyl-4-((4-methylpyrimidin-2-yl)methoxy)-2H-[1,4'-bipyridin]-2-one |

| No. | Structure | Compound Name |
|---|---|---|
| 30 | 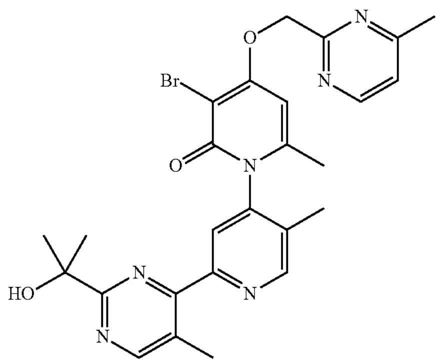 [SMILES: Cc1ccnc(COc2cc(C)n(-c3cc(-c4nc(C(C)(C)O)ncc4C)ncc3C)c(=O)c2Br)n1] | 3-bromo-2'-(2-(2-hydroxypropan-2-yl)-5-methylpyrimidin-4-yl)-5',6-dimethyl-4-((4-methylpyrimidin-2-yl)methoxy)-2H-[1,4'-bipyridin]-2-one |
| 31 | 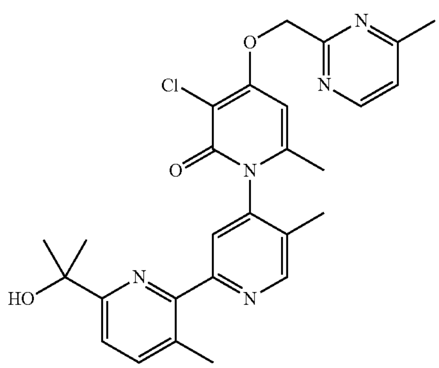 [SMILES: Cc1ccnc(COc2cc(C)n(-c3cc(-c4nc(C(C)(C)O)ccc4C)ncc3C)c(=O)c2Cl)n1] | 3-chloro-6''-(2-hydroxypropan-2-yl)-3'',5',6-trimethyl-4-((4-methylpyrimidin-2-yl)methoxy)-2H-[1,4':2',2''-terpyridin]-2-one |
| 32 | 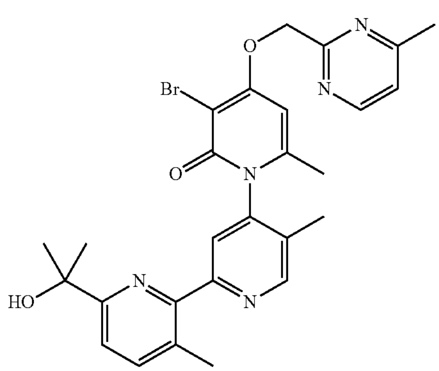 [SMILES: Cc1ccnc(COc2cc(C)n(-c3cc(-c4nc(C(C)(C)O)ccc4C)ncc3C)c(=O)c2Br)n1] | 3-bromo-6''-(2-hydroxypropan-2-yl)-3'',5',6-trimethyl-4-((4-methylpyrimidin-2-yl)methoxy)-2H-[1,4':2',2''-terpyridin]-2-one |

C. General Synthetic Schemes

The compounds of the present invention can be prepared using the methods illustrated in the general synthetic schemes and experimental procedures detailed below. These general synthetic schemes and experimental procedures are presented for purposes of illustration and are not intended to be limiting. The starting materials used to prepare the compounds of the present invention are commercially available or can be prepared using routine methods known in the art.

Representative procedures for the preparation of compounds of invention are outlined in Schemes 1 and 2. The substituted pyridine starting material can be purchased or prepared using methods known in the art. Scheme 1 highlights the synthesis of the fully elaborated 1,4'-bipyridin-2-ones. The synthesis of pyridinone 1c can be accomplished by reaction of acetal 1a and pyridine 1b in a solvent such as dioxane. Alkylation of the phenol of 1c with the desired benzyl substituent (A) gives benzylated 1d. Reaction of 1d with a vinyl tin reagent in the presence of a palladium catalyst provides methyl ketone 1e. Halogenation of 1e using N-chlorosuccinimide (or N-bromosuccinimide if the corresponding bromo is desired) in a solvent such as isopropanol provides 1f. In situ enamine formation by reaction of 1f with N,N-dimethylformamide dimethyl acetal provides an intermediate, which is then reacted with 2-hydroxy-2-methylpropionamidine in a solvent such as DMF to give pyridin-one 1g.

Scheme 1:

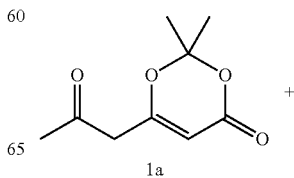

1a

-continued

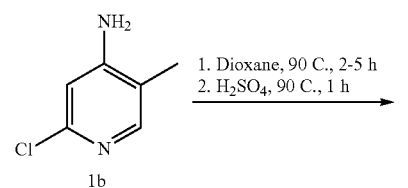
1b

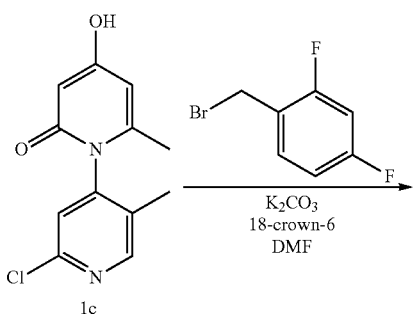
1c

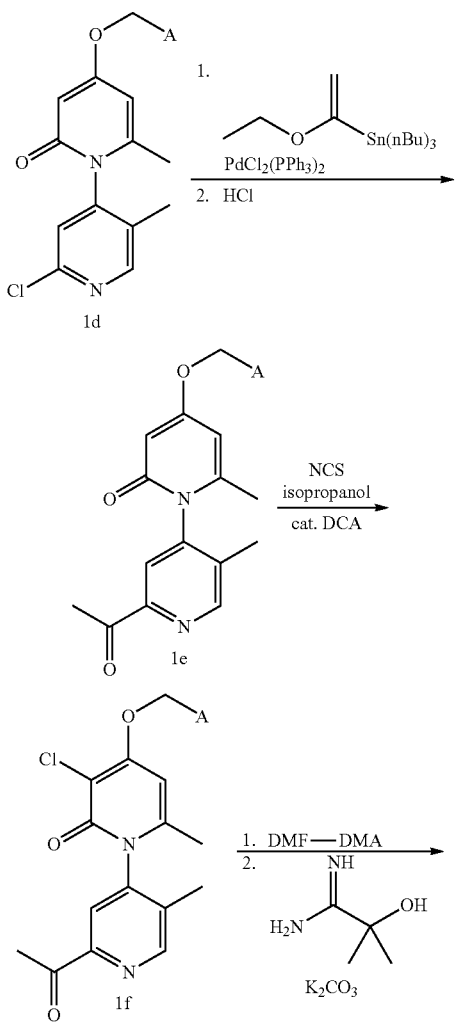

-continued

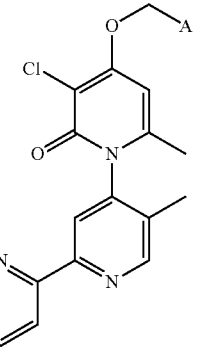
1g

A = 2,4-difluoro-3-methylphenyl, 2,4-difluoro-5-methylphenyl, 5-methylpyridin-3-yl, or 4-methylpyrimidin-2-yl The synthesis of the desired compounds wherein the benzyl substituent A is added in the last step is shown in Scheme 2. Pyridinone 2c can be accomplished by reaction of acetal 2a and pyridine 2b in a solvent such as dioxane as described in Scheme 1. Protection of the phenol of 2c with para-methoxybenzyl bromide gives benzylated 2d. Reaction of 2d with a vinyl tin reagent in the presence of a palladium catalyst provides methyl ketone 2e. Halogenation of 1e using N-chlorosuccinimide (or N-bromosuccinimide if the corresponding bromo is desired) in a solvent such as isopropanol provides 2f. In situ enamine formation by reaction of 2f with N,N-dimethylformamide dimethyl acetal provides an intermediate, which is then reacted with 2-hydroxy-2-methylpropionamidine in a solvent such as DMF to give pyrimidinone 2g. Deprotection of the benzyl group by treating 2g with an acid such as TFA or HCl provides 2h. Alkylation of phenol 2h with the desired benzyl halide substituent (ACH2X) provides the desired pyridinones 2i.

Scheme 2:

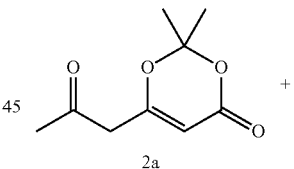
2a

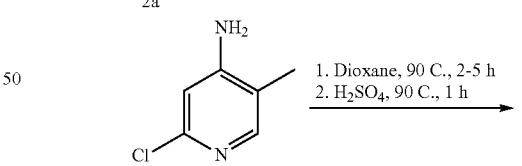
2b

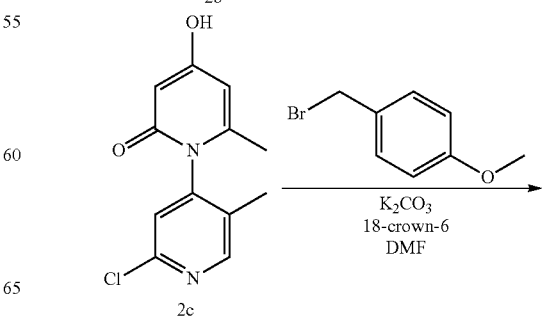
2c

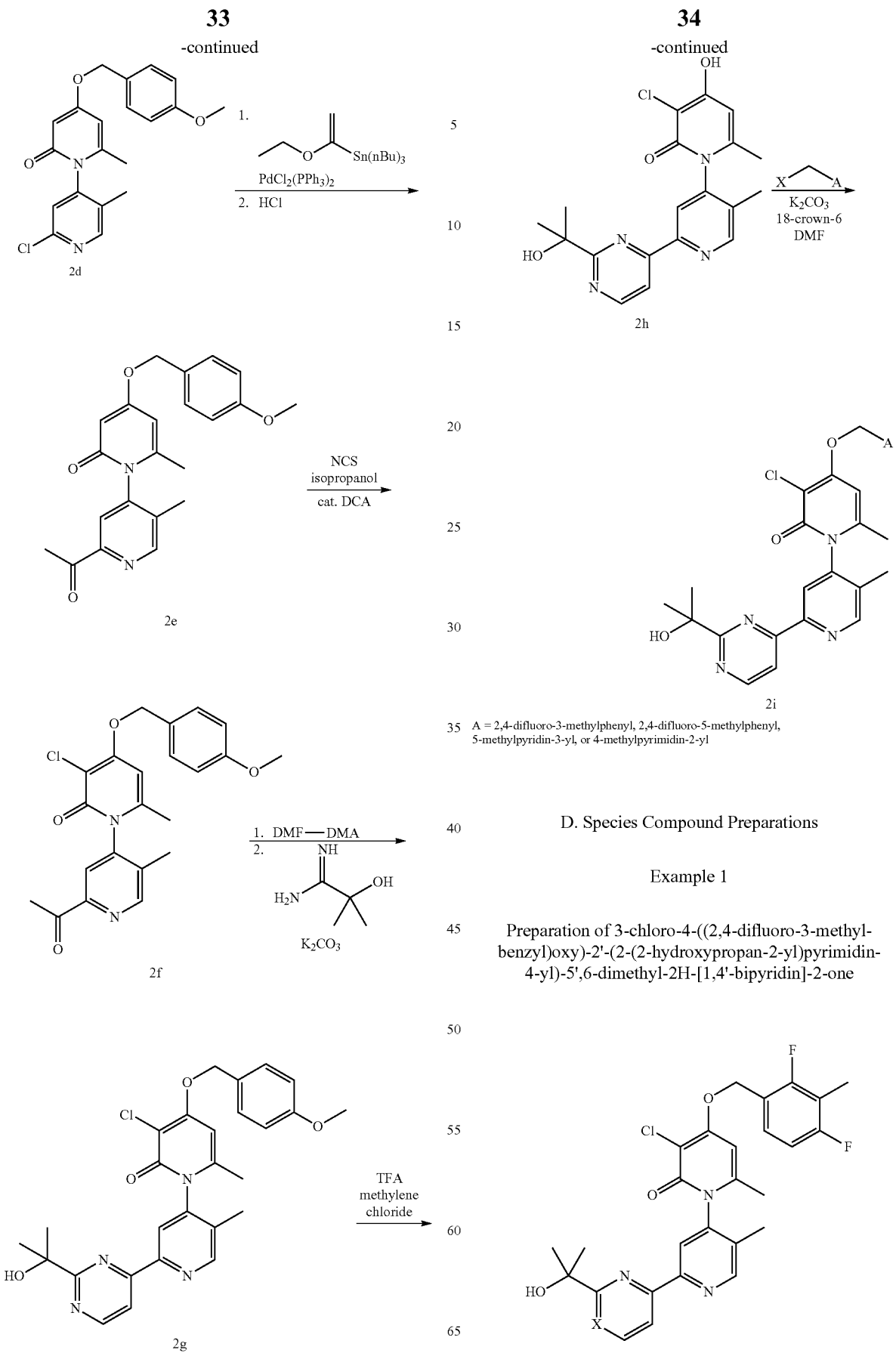
A = 2,4-difluoro-3-methylphenyl, 2,4-difluoro-5-methylphenyl, 5-methylpyridin-3-yl, or 4-methylpyrimidin-2-yl
D. Species Compound Preparations
Example 1
Preparation of 3-chloro-4-((2,4-difluoro-3-methyl-benzyl)oxy)-2'-(2-(2-hydroxypropan-2-yl)pyrimidin-4-yl)-5',6-dimethyl-2H-[1,4'-bipyridin]-2-one

Step A: Preparation of 2'-chloro-4-hydroxy-6,5'-dimethyl-[1,4']bipyridinyl-2-one

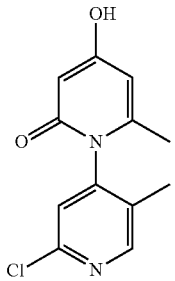

To a screw top vial with rubber septa inset was added 2,2-dimethyl-6-(2-oxo-propyl)-[1,3]dioxin-4-one, prepared as described in Organic Letters, 11(21), 4910-4913; 2009, (500 mg, 2.7 mmol) and 2-chloro-5-methyl-pyridin-4-ylamine (575 mg, 4 mmol, 1.5 eq). The mixture was dissolved in anhydrous 1,4-dioxane (10 mL). Once the mixture was homogeneous the vial was placed on a stirrer/hot plate preset to 90° C. The reaction was heated at this temperature for 3.5 h. The reaction was removed from heat and analyzed by HPLC which showed the reaction was >95% complete. The vial was placed back on the hot plate. To the heated mixture was added $H_2SO_4$ (250 μL) and the reaction was heated for 1 h. The reaction was removed from the heat and after cooling to ambient temperature, the dioxane was removed by passing a stream of air over the top of the open vial to give a brown residue. Water (~4 mL) was added to the vial, which was stirred for 30 min. The resulting tan solid was filtered off with washing from additional water and the diethyl ether to give the desired product (531 mg, 57% based on being the sulfate salt) as a tan solid which by HPLC was ~95% pure: MS (M+H) 250.

Step B: Preparation of 2'-chloro-4-((4-methoxybenzyl)oxy)-5',6-dimethyl-2H-[1,4'-bipyridin]-2-one

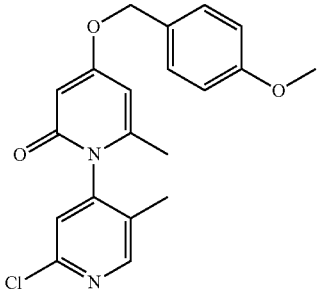 [SMILES: COc1ccc(COc2cc(C)n(-c3cc(Cl)ncc3C)c(=O)c2)cc1]

To a solution of 2'-chloro-4-hydroxy-6,5'-dimethyl-[1,4']bipyridinyl-2-one of part A (1.5 g, 6.0 mmol) in N,N-dimethylformamide (10 mL) was added 4-methoxybenzylbromide (1.33 g, 6.6 mmol), potassium carbonate (2.1 g, 15.1 mmol) and 18-crown-6 (40 mg). The slurry was stirred at ambient temperature for 18 hours. The reaction was partitioned between ethyl acetate and water. The organic layer was washed with water and brine and dried over magnesium sulfate. The solution was concentrated in vacuo to provide a brown oil. Normal phase chromatography (ethyl acetate/heptane) provided the alkylated product (1.37 g): MS (M+H) 372.

Step C: Preparation of 2'-acetyl-4-((4-methoxybenzyl)oxy)-5',6-dimethyl-2H-[1,4'-bipyridin]-2-one

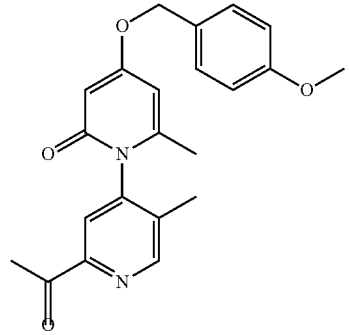

A solution of 2'-chloro-4-((4-methoxybenzyl)oxy)-5',6-dimethyl-2H-[1,4'-bipyridin]-2-one of part B (1.19 g, 3.2 mmol), tributyl(1-ethoxyvinyl)tin (1.2 mL, 3.5 mmol) and $PdCl_2(PPh_3)_2$ (22 mg, 0.032 mmol) in 1,4-dioxane (10 mL) was irradiated using a CEM Explorer™ microwave at 120° C. for 1.5 hours. The resulting dark solution was filtered through Celite, rinsing with ethyl acetate. The filtrate was concentrated and the residue was dissolved into tetrahydrofuran (5 mL) and treated with concentrated HCl until hydrolysis was complete. The solution was concentrated in vacuo and purified using normal phase chromatography (ethyl acetate/heptane) to provide the acetyl compound (700 mg): MS (M+H) 379.

Step D: Preparation of 2'-acetyl-3-chloro-4-((4-methoxybenzyl)oxy)-5',6-dimethyl-2H-[1,4'-bipyridin]-2-one

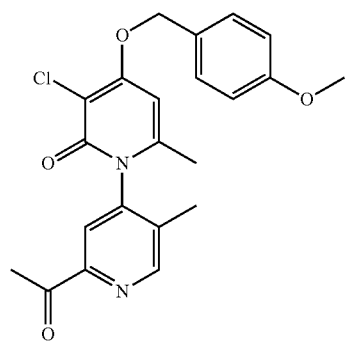 [SMILES: COc1ccc(COc2cc(C)n(-c3cc(C(C)=O)ncc3C)c(=O)c2Cl)cc1]

To a solution of 2'-acetyl-4-((4-methoxybenzyl)oxy)-5',6-dimethyl-2H-[1,4'-bipyridin]-2-one of part C (689 mg, 1.82 mmol) in 2-propanol (15 mL) was added N-chlorosuccinimide (266 mg, 2.00 mmol) and 3 drops of dichloroacetic acid. The slurry was heated at 60° C. for 3 hours. The solution was cooled using an ice bath and the resulting white solid was collected by vacuum filtration. The filtrate was partitioned between ethyl acetate and water. The organic layer was washed with water and brine and dried over magnesium sulfate. The solution was concentrated in vacuo and purified using normal phase chromatography (ethyl acetate/heptane) and the desired product was combined with material obtained via filtration (568 mg): MS (M+H) 414.

Step E: Preparation of 3-chloro-2'-(2-(2-hydroxypropan-2-yl)pyrimidin-4-yl)-4-((4-methoxybenzyl)oxy)-5',6-dimethyl-2H-[1,4'-bipyridin]-2-one

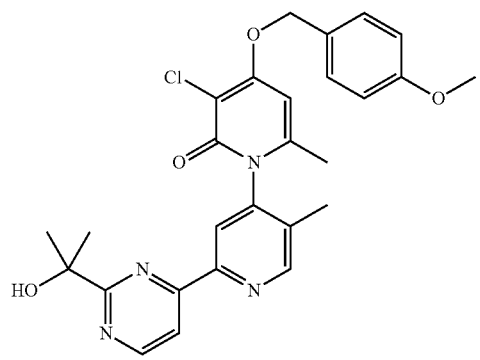 [SMILES: COc1ccc(COc2cc(C)n(-c3cc(-c4ccnc(C(C)(C)O)n4)ncc3C)c(=O)c2Cl)cc1]

To a solution of 2'-acetyl-3-chloro-4-((4-methoxybenzyl)oxy)-5',6-dimethyl-2H-[1,4'-bipyridin]-2-one of step D (562 mg, 1.36 mmol) in N,N-dimethylformamide (5 mL) was added N,N-dimethylformamide dimethyl acetal (0.27 mL, 2.04 mmol) and the solution was heated to 55° C. for 18 hours. The solution was concentrated to half volume and partitioned between ethyl acetate and brine. The organic layer was dried over magnesium sulfate and concentrated to provide the crude enamine intermediate as an orange oil. The enamine was dissolved into N,N-dimethylformamide (7 mL) and 2-hydroxy-2-methylpropionamidine HCl (280 mg, 2.04 mmol) and potassium carbonate (563 mg, 4.08 mmol) were added. The slurry was heated at 75° C. for eighteen hours. The slurry was returned to ambient temperature and partitioned between ethyl acetate and water. The organic layer was washed with brine and dried over magnesium sulfate. The solution was concentrated and purified using normal phase chromatography (ethyl acetate/heptane) to provide the title compound as a light yellow solid (320 mg, 46%): MS (M+H) 508.

Step F: Preparation of 3-chloro-4-hydroxy-2'-(2-(2-hydroxypropan-2-yl)pyrimidin-4-yl)-5',6-dimethyl-2H-[1,4'-bipyridin]-2-one

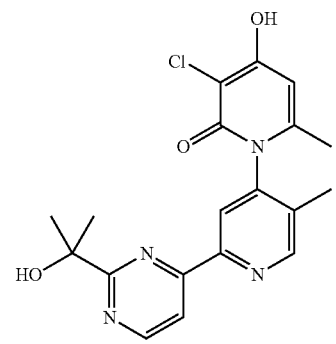 [SMILES: Cc1cnc(-c2ccnc(C(C)(C)O)n2)cc1-n1c(C)cc(O)c(Cl)c1=O]

To a solution of 3-chloro-2'-(2-(2-hydroxypropan-2-yl)pyrimidin-4-yl)-4-((4-methoxybenzyl)oxy)-5',6-dimethyl-2H-[1,4'-bipyridin]-2-one (2.53 g, 5.00 mmol) in dichloromethane (20 mL) was added trifluoroacetic acid (1.0 mL). The solution was stirred for several hours at room temperature. The solution was concentrated, diluted with water and extracted several times with ethyl acetate. The combined organic layers were dried (MgSO$_4$), filtered and concentrated to provide 1.7 g of the title compound: MS (M+H) 388.

Step G: Preparation of 3-chloro-4-((2,4-difluoro-3-methylbenzyl)oxy)-2'-(2-(2-hydroxypropan-2-yl)pyrimidin-4-yl)-5',6-dimethyl-2H-[1,4'-bipyridin]-2-one

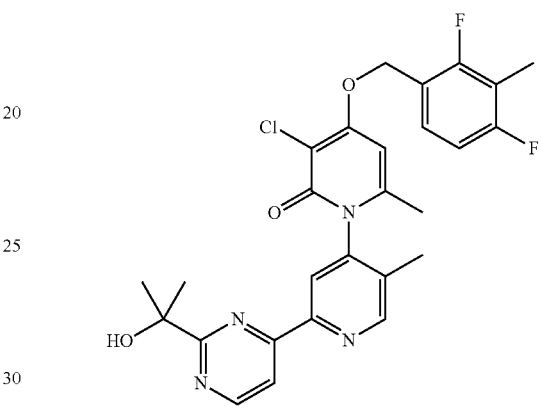

To a solution of 3-chloro-4-hydroxy-2'-(2-(2-hydroxypropan-2-yl)pyrimidin-4-yl)-5',6-dimethyl-2H-[1,4'-bipyridin]-2-one (386 mg, 1.0 mmol) in N,N-dimethylformamide (1.7 mL) was added 1-(bromomethyl)-2,4-difluoro-3-methylbenzene (243 mg, 1.1 mmol), potassium carbonate (0.35 g, 2.52 mmol) and 18-crown-6 (7 mg). The slurry was stirred at ambient temperature for 18 hours. The reaction was partitioned between ethyl acetate and water. The organic layer was washed with water and brine and dried over magnesium sulfate. The solution was concentrated in vacuo to provide a brown oil. Normal phase chromatography (ethyl acetate/heptane) provided 319 mg of the alkylated product: MS (M+H) 528.

Example 17

Preparation of 3-chloro-2'-(2-(2-hydroxypropan-2-yl)pyrimidin-4-yl)-5',6-dimethyl-4-((5-methylpyridin-3-yl)methoxy)-2H-[1,4'-bipyridin]-2-one

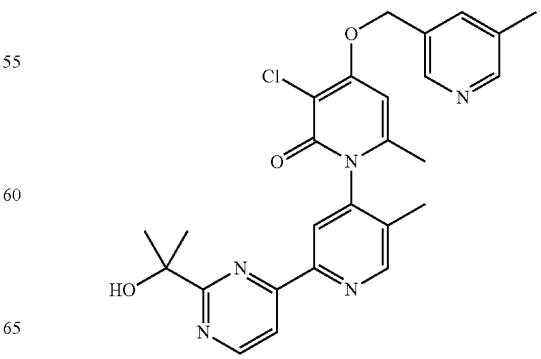

To the intermediate at Step F, a solution of 3-chloro-4-hydroxy-2'-(2-(2-hydroxypropan-2-yl)pyrimidin-4-yl)-5',6-dimethyl-2H-[1,4'-bipyridin]-2-one (386 mg, 1.0 mmol) in N,N-dimethylformamide (1.7 mL) was added 3-(bromomethyl)-5-methylpyridine (205 mg, 1.1 mmol), potassium carbonate (0.35 g, 2.52 mmol) and 18-crown-6 (7 mg). The slurry was stirred at ambient temperature for 18 hours. The reaction was partitioned between ethyl acetate and water. The organic layer was washed with water and brine and dried over magnesium sulfate. The solution was concentrated in vacuo to provide a brown oil. Normal phase chromatography (ethyl acetate/heptane) provided 351 mg of the alkylated product MS (M+H) 493.

E. Methods of Treatment

The present disclosure further provides methods for treating a condition in a subject having or susceptible to having such a condition, by administering to the subject a therapeutically-effective amount of one or more compounds as described above. In one embodiment, the treatment is preventative treatment. In another embodiment, the treatment is palliative treatment. In another embodiment, the treatment is restorative treatment.

1. Conditions

The conditions that can be treated in accordance with the present invention include, but are not limited to, autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, lymphoma and the like.

In some embodiments the methods described herein are used to treat patients with disorders arising from dysregulated cytokine, enzymes and/or inflammatory mediator production, stability, secretion, posttranslational processing. Examples of cytokines that may be dysregulated include interleukins 1, 2, 6, 8, 10, 12, 17, 22 and 23 along with tumor necrosis factor alpha and interferons alpha, beta and gamma. Examples of inflammatory mediators that may be dysregulated include nitric oxide, prostaglandins and leukotrienes. Examples of enzymes include cyclo-oxygenase, nitric oxide synthase and matrixmetalloprotease.

In some embodiments the methods described herein are used to treat patients with dysregulated p38 activity, activation, biosynthesis or pathway function.

In some embodiments, the methods described herein are used to treat a patient in need thereof suffering from an autoimmune disorder, chronic and/or acute inflammatory disorder and/or auto-inflammatory disorder. Examples of disorders include, but are not limited to colitis, multiple sclerosis, arthritis, rheumatoid arthritis, osteoarthritis, juvenile arthritis, psoriatic arthritis, cryopyrin associated periodic syndromes, Muckle-Wells Syndrome, Familial Cold Auto-inflammatory Syndrome, neonatal-onset multisystem inflammatory disease, TNF receptor associated periodic syndrome, acute pancreatitis, chronic pancreatitis, atherosclerosis, inflammatory bowel disease, Crohn's disease, ulcerative colitis, Diabetes mellitus type 1, Diabetes mellitus type 2, diabetic retinopathy, Still's disease, multiple sclerosis, vasculitis, sarcoidosis, pulmonary inflammation, acute respiratory distress syndrome, wet and dry age-related macular degeneration, autoimmune hemolytic syndromes, autoimmune hepatitis, autoimmune neuropathy, autoimmune ovarian failure, autoimmune orchitis, autoimmune thrombocytopenia, reactive arthritis, ankylosing spondylitis, silicone implant associated autoimmune disease, Sjogren's syndrome, Familial Mediterranean Fever, systemic lupus erythematosus, vasculitis syndromes (such as, for example, giant cell arteritis, Behcet's disease & Wegener's granulomatosis), Vitiligo, secondary hematologic manifestation of autoimmune diseases (such as, for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (including, for example, Meniere's disease), Goodpasture's syndrome, Graves' disease, HW-related autoimmune syndromes and Gullain-Barre disease; Examples of inflammatory conditions include, but are not limited to sepsis, septic shock, endotoxic shock, exotoxin-induced toxic shock, gram negative sepsis, toxic shock syndrome, glomerulonephritis, peritonitis, interstitial cystitis, psoriasis, atopic dermatitis, hyperoxia-induced inflammations, asthma, chronic obstructive pulmonary disease (COPD), vasculitis, graft vs. host reaction (i.e., graft vs. host disease), allograft rejections (e.g., acute allograft rejection, and chronic allograft rejection), early transplantation rejection (e.g., acute allograft rejection), reperfusion injury, acute pain, chronic pain, neuropathic pain, Fibromyalgia, pancreatitis, chronic infections, meningitis, encephalitis, myocarditis, gingivitis, post surgical trauma, tissue injury, traumatic brain injury, hepatitis, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis. Fibrotic diseases; Metabolic disorders, including but not limited Obesity, steroid-resistance, glucose intolerance, metabolic syndrome. In some embodiments, the methods described herein can be used to treat a patient in need thereof and suffering from neoplasia. Examples of these conditions include but not limited to angiogenesis, multiple myeloma, leukemia, B cell lymphoma, T cell lymphoma, mast cell tumors, lymphoma, Hodgkin's disease, cancer of the bone, mouth/pharynx, oesophagus, larynx, stomach, intestine, colon, rectum, lung, liver, pancreas, nerve, brain, head and neck, throat, ovary, uterus, prostate, testis, bladder, kidney, breast non-small cell lung carcinoma, melanoma, skin cancer, teratoma, rhabdomyosarcoma, glioma, metastatic and bone disorders. In some embodiments, the disease associated with dysregulated p38 include Cardiovascular and Cerebrovascular diseases, including but not limited to Atherosclerosis, restenosis of an atherosclerotic coronary artery, Acute coronary syndrome, myocardial infarction, cardiac-allograft vasculopathy and stroke; central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy. The term patient refers to both humans and nonhuman animals with the abovementioned conditions. Nonhuman animals could be companion animals such as, but not limited to canine and feline species.

2. Subjects

Suitable subjects to be treated according to the present invention include mammalian subjects. Mammals according to the present invention include, but are not limited to, human, canine, feline, bovine, caprine, equine, ovine, porcine, rodents, lagomorphs, primates, and the like, and encompass mammals in utero. Subjects may be of either gender and at any stage of development.

3. Administration and Dosing

The compounds of the present invention are generally administered in a therapeutically effective amount.

The compounds of the present invention can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 30 mg/kg/day, in single or divided doses. Depending on age, species and condition being treated, dosage levels below the lower limit of this range may be suitable. In other cases, still larger doses may be used without harmful side effects. Larger doses may also be divided into several smaller doses, for administration throughout the day.

F. Pharmaceutical Compositions

For the treatment of the conditions referred to above, the compounds of described herein can be administered as follows:

Oral Administration

The compounds of the present invention may be administered orally, including by swallowing, so that the compound enters the gastrointestinal tract, or absorbed into the blood stream directly from the mouth (e.g., buccal or sublingual administration).

Suitable compositions for oral administration include solid formulations such as tablets, lozenges and capsules, which can contain liquids, gels, or powders.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable lubricants, for use in a tablet, may be present in amounts from about 0.1% to about 5% by weight, and include calcium, zinc or magnesium stearate, sodium stearyl fumarate and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet, may be present in amounts from about 0.1% to about 3% by weight, and include polysorbate 80, sodium dodecyl sulfate, talc and silicon dioxide.

Parenteral Administration

Compounds of the present invention may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

Compounds of the present invention may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

G. Combinations and Combination Therapy

The compounds of the present invention can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers and inhibitors of cell adhesion molecules.

p38 inhibitor compositions described herein are also optionally used in combination with other therapeutic reagents that are selected for their therapeutic value for the condition to be treated In general, the compositions described herein and, in embodiments where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified. In certain instances, it is appropriate to administer a p38 inhibitor composition as described herein in combination with another therapeutic agent. By way of example only, if one of the side effects experienced by a patient upon receiving a p38 inhibitor composition as described herein is rash, then it is appropriate to administer an anti-histamine agent in combination with the initial therapeutic agent. Or, by way of example only, the therapeutic effectiveness of a p38 inhibitor is enhanced by administration of another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a p38 inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

In another embodiment, a p38 inhibitor is optionally used in combination with procedures that provide additional or synergistic benefit to the patient. A p38 inhibitor and the additional therapy(ies) are optionally administered before, during or after the occurrence of a disease or condition, and the timing of administering the composition containing a p38 inhibitor varies in some embodiments. Thus, for example, a p38 inhibitor is used as a prophylactic and is administered continuously to subjects with a propensity to develop conditions or diseases in order to prevent the occurrence of the disease or condition. A p38 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A p38 inhibitor can be used in combination with drugs from the following classes: NSAIDs, immunosuppressive drugs, immunomodulatory drugs, cytostatic drugs, anti-proliferative agents, angiogenesis inhibitors, biological agents, steroids, vitamin D3 analogs, retinoids, other kinase inhibitors, cytokine blockers, corticosteroids and inhibitors of cell adhesion molecules. Where a subject is suffering from or at risk of suffering from atherosclerosis or a condition that is associated with atherosclerosis, a p38 inhibitor composition described herein is optionally used together with one or more agents or methods for treating atherosclerosis or a condition that is associated with atherosclerosis in any combination. Examples of therapeutic agents/treatments for treating atherosclerosis or a condition that is associated with atherosclerosis include, but are not limited to any of the following: torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol and clofibrate.

Where a subject is suffering from or at risk of suffering from an inflammatory condition, a p38 inhibitor composition described herein is optionally used together with one or more agents or methods for treating an inflammatory condition in any combination. Examples of therapeutic agents/treatments for treating an autoimmune and/or inflammatory condition include, but are not limited to any of the following: corticosteroids, nonsteroidal antiinflammatory drugs (NSAID) (e.g. ibuprofen, naproxen, acetaminophen, aspirin, Fenoprofen (Nalfon), Flurbiprofen (Ansaid), Ketoprofen, Oxaprozin (Daypro), Diclofenac sodium (Voltaren), Diclofenac potassium (Cataflam), Etodolac (Lodine), Indomethacin (Indocin), Ketorolac (Toradol), Sulindac (Clinoril), Tolmetin (Tolectin), Meclofenamate (Meclomen), Mefenamic acid (Ponstel), Nabumetone (Relafen), Piroxicam (Feldene), cox-2 inhibitors (e.g., celecoxib (Celebrex))), immunosuppressants (e.g., methotrexate (Rheumatrex), leflunomide (Arava), azathioprine (Imuran), cyclosporine (Neoral, Sandimmune), tacrolimus and cyclophosphamide (Cytoxan), CD20 blockers (Rituximab), Tumor Necrosis Factor (TNF) blockers (e.g., etanercept (Enbrel), infliximab (Remicade) and adalimumab (Humira)), Abatacept (CTLA4-Ig) and interleukin-1 receptor antagonists (e.g. Anakinra (Kineret), interleukin 6 inhibitors (e.g., Actemra), interleukin 17 inhibitors (e.g., AIN457), Janus kinase inhibitors (e.g., Tasocitinib), syk inhibitors (e.g. R788), chloroquine and its derivatives.

For use in cancer and neoplastic diseases a p38 inhibitor is optimally used together with one or more of the following classes of drugs: wherein the anti-cancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, proteosome inhibitor, chemotherapy agent, or glucose reduction agent.

EXAMPLES

P38 inhibitory potency and P38/MK2 substrate selectivity: The novel, MK2 substrate-selective inhibitory mechanism of compounds is evaluated in enzyme assays comparing inhibitor potency in blocking p38/MK2 versus p38/PRAK induced phosphorylation of an HSP-27 derived peptide substrate. The ability of compounds to inhibit activated phospho-p38α is evaluated using a p38α/MK2 and a p38α/PRAK cascade assay format. The kinase activity of p38α is determined by its ability to phosphorylate GST-MK2 or GST-PRAK. Activation of MK2 or PRAK by p38α is quantitated by measuring the phosphorylation of a fluorescently-labeled, MK2 specific peptide substrate, Hsp27 peptide (FITC-KKKALSRQLS-VAA). The phosphorylation of the Hsp27 peptide is quantified using the Caliper LabChip 3000. Kinase reactions is carried out in a 384-well plate (Matrical, MP101-1-PP) in 20 mM HEPES pH 7.5, 10 mM MgCl2, 0.0005% Tween-20, 0.01% BSA, 1 mM DTT, and 2% DMSO. The inhibitor concentration is varied between 0.02-30,000 nM, while the Hsp27 peptide substrate and MgATP are held constant at 1 µM and 10 µM, respectively. Activated p38α is added to a final concentration of 20 pM for reactions with nonphosphorylated 1 nM His6-MK2 in the cascade reaction. For the p38α/PRAK cascade, unactivated GST-PRAK is held constant at 1 nM while p38α is added in to a final concentration of 20 pM. Kinase reactions are incubated at room temperature and quenched after 30 minutes by the addition of stop buffer (180 mM HEPES, 30 mM EDTA, and 0.2% Coating Reagent-3). Under these conditions, approximately 20% of the substrate Hsp27 peptide is phosphorylated. Reactions are initiated by the addition of activated p38α except for preincubation experiments, where reactions are initiated by the addition of Hsp27 peptide and MgATP. Preincubation of p38α with inhibitor or p38α with unactivated His6-MK2 or unactivated GST-PRAK and inhibitor are performed at 2× final assay concentrations at room temperature 240 minutes prior to adding ATP and Hsp27 peptide to initiate catalysis. The p38α compound inhibitory potency is quantitated from dose-response IC50 values or Ki values from p38α/MK2 cascade assays while the substrate selectivity is calculated as a ratio of p38α/PRAK:p38α/MK2 IC50 values. Species compounds of Formula (I), described hereinabove, evaluated in this assay, are expected to provide a therapeutic benefit in the treatment of p38 kinase mediated diseases, such as autoimmune diseases and lymphoma.

Cytokine regulation in human monocytes: The p38 pathway has been shown to be critical for the biosynthesis of a number of proinflammatory cytokines including TNFα, IL-1β and IL-6. Evaluation of the potency and efficacy of p38 inhibitors to block cytokine production is carried out using the human U937 cell line. The U937 human pre-monocytic cell line is obtained from the American Type Culture Collection (Rockville, Md.). These cells are differentiated to a monocytic/macrophage phenotype as described by Burnette (Burnette et al, (2009). SD0006: a potent, selective and orally available inhibitor of p38 kinase, *Pharmacology* 84(1):42-60). Differentiated U937 cells are seeded into 96-well tissue culture plates (200,000 cells/well) in complete media. After 24 hours, the cells are pretreated for 60 minutes in the presence or absence of compound and then stimulated with LPS (0.1 µg/mL) for 4 hours. Culture media are then collected for determination of TNFα, IL-6 or IL-1β levels by ELISA. Cytokine concentrations are extrapolated from recombinant protein standard curves using a four-parameter logistic model and solving for $IC_{50}$ after iterating to the best least-squares fit. Species compounds of Formula (I), described hereinabove, evaluated in this assay, are expected to provide a therapeutic benefit in the treatment of p38 kinase mediated diseases, such as lymphoma or inflammation.

IL1β induced prostaglandin production in rheumatoid arthritis synovial fibroblasts (RASF): Rheumatoid arthritis synovial fibroblasts (RASF) are derived from the inflamed synovium of a female RA patient who was undergoing total knee replacement. Synovial tissue is teased away from adjacent cartilage and dispersed into single cells with collagenase. Cells are expanded and banked. RASF cells are further cultured as described by Burnette supra. RASF cells are seeded into 96-well tissue culture plates ($5\times10^4$ cells/well) in complete growth medium. After 24 hours, the medium is replaced with fresh growth medium containing 1% FBS. Cells are treated with serial concentrations (30,000-0.01 nM) of compound or dimethyl-sulfoxide (DMSO) vehicle control for 1 hour then stimulated with 1 ng/mL IL-1β (R&D Systems, Minneapolis, Minn.) for 18-20 hours at 37° C. and conditioned media collected. $PGE_2$ levels the in cultured media are quantitated by ELISA (Cayman Chemical, Ann Arbor, Mich.). Species compounds of Formula (I), described hereinabove, evaluated in this assay, are expected to provide a therapeutic benefit in the treatment of p38 kinase mediated diseases, such as lymphoma or rheumatoid arthritis.

Substrate selectivity in HUVEC cells: When a compound is identified from the biochemical characterization step with selective inhibition of p38/MK2, it is next placed into a cell-based assay to verify enzyme to cell translatability. These assays utilize human umbilical vein endothelial cells (HUVEC) to demonstrate inhibition of Hsp27 phosphorylation (a biomarker of p38/MK2 activation) while sparing production of tissue factor (TF), which is linked to another downstream substrate of p38, MSK. In a 96-well format, adherent HUVEC (at 5 passages or less) are treated for 1 hour with serially-diluted compounds, including a non-selective p38 inhibitor as a reference, or vehicle for controls. For Hsp27 phosphorylation, cells are then stimulated with 500 pg/mL IL-1β for 0.5 hours, media is removed, cells are lysed, and phospho-Hsp27 in the lysate is quantitated by enzyme-linked immunosorbent assay (ELISA)(Life Technologies, Carlsbad, Calif.). The procedure for TF release is a similar ELISA-based assay (American Diagnostica, Stanford, Conn.), except that IL-1β stimulation proceeds for 5 hours. The ratio of TF inhibition IC50:HSP27 phosphorylation inhibition IC50 is defined as the substrate selectivity index in these cells. Species compounds of Formula (I), described hereinabove, evaluated in this assay, are expected to provide a therapeutic benefit in the treatment of p38 kinase mediated diseases, such as lymphoma and autoinflammatory disease.

Canine B cell growth regulation: p38 inhibitors have been shown to uniquely inhibit canine B cell proliferation and survival. This selective effect on canine B cells may be exploited in therapeutic treatment for canine B cell lymphoma, a fatal disease that impacts>40,000 companion animals in the United States. Quantitation of impact of p38 inhibitors on B cell growth is a cellular indicator of efficacy in B cell lymphoma. Species compounds of Formula (I), described hereinabove, evaluated in this assay, are expected to provide a therapeutic benefit in the treatment of p38 kinase mediated diseases, such as lymphoma. These assays utilize beagle dog spleens obtained with protocols approved by the Saint Louis University Animal Care and Use Committee in collaboration with Seventh Wave Laboratories. Leukocytes are isolated from splenocytes by centrifugation through Histopaque 1077. To evaluate effect on proliferation, leukocytes are then cultured for 48 hours in 96-well plates in the presence of vehicle or test compounds. Cells are stimulated with LPS for TLR4 stimulation, *Staphylococcus aureus* B cell mitogen, or concanavalin-A T cell mitogen, then proliferation is quantitated with a BRDU incorporation ELISA (Roche, Mannheim, Germany). For apoptosis experiments, leukocytes are plated on 96-well polypropylene U bottom plates and treated with p38 MAPK inhibitors or staurosporine (as a positive control) for up to 24 hours in the absence or presence of actinomycin D or cycloheximide (if needed to increase apoptosis rate). Apoptosis is determined using Caspase-Glo 3/7 luminescent assay (Promega, Madison, Wis.). In both assays, values generated after incubation with increasing concentrations of the inhibitors are compared to a negative control without inhibitors.

LPS Induced TNFα Production in rats: Rats are fasted eighteen hours prior to oral dosing, and allowed free access to water throughout the experiment. Each treatment group consists of five animals. Compounds are prepared as a suspension in a vehicle consisting of 0.5% methylcellulose, (Sigma Aldrich, St. Louis, Mo.), 0.025% Tween 20 (Sigma Aldrich). The compound or vehicle is administered by oral gavage in a volume of 1 mL. Two vehicle groups are used per experiment to control for intra-experiment variability. LPS (*E. coli* serotype 0111:B4, Sigma Aldrich) is administered four hours after compound intravenous injection at a dose of 1 mg/kg in 0.5 mL sterile saline (Baxter Healthcare, Deerfield, Ill.). Blood is collected in serum separator tubes via cardiac puncture ninety minutes after LPS injection, a time point corresponding to maximal TNFα and IL-1β production. After clotting, serum is withdrawn and stored at −20° C. and IL-1β and TNFα levels quantitated by ELISA (Burnette supra). Species compounds of Formula (I), described hereinabove, evaluated in this assay, are expected to provide a therapeutic benefit in the treatment of p38 kinase mediated diseases, such as lymphoma or inflammation.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:

1. A compound of Formula (I):

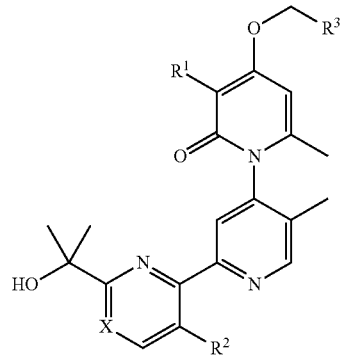

(I)

or a pharmaceutically acceptable salt thereof, wherein:

X is CH or N;

$R^1$ is chloro or bromo;

$R^2$ is —H or methyl; and $R^3$ is selected from the group consisting of 2,4-difluoro-3-methylphenyl, 2,4-difluoro-5-methylphenyl, 5-methylpyridin-3-yl, and 4-methylpyrimidin-2-yl.

2. Compound according to claim 1 of Formula (II):

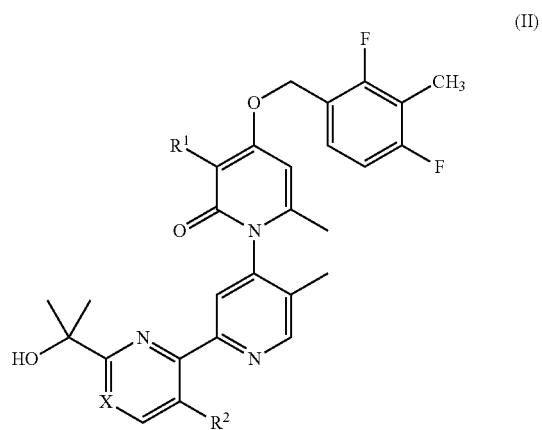

(II)

or a pharmaceutically acceptable salt thereof, wherein:

X is CH or N;

$R^1$ is chloro or bromo; and $R^2$ is —H or methyl.

3. Compound according to claim 2 selected from the group consisting of:

3-chloro-4-((2,4-difluoro-3-methylbenzyl)oxy)-2'-(2-(2-hydroxypropan-2-yl)pyrimidin-4-yl)-5',6-dimethyl-2H-[1,4'-bipyridin]-2-one;

3-bromo-4-((2,4-difluoro-3-methylbenzyl)oxy)-2'-(2-(2-hydroxypropan-2-yl)pyrimidin-4-yl)-5',6-dimethyl-2H-[1,4'-bipyridin]-2-one;

3-chloro-4-((2,4-difluoro-3-methylbenzyl)oxy)-6"-(2-hydroxypropan-2-yl)-5',6-dimethyl-2H-[1,4':2',2"-terpyridin]-2-one;

3-bromo-4-((2,4-difluoro-3-methylbenzyl)oxy)-6"-(2-hydroxypropan-2-yl)-5',6-dimethyl-2H-[1,4':2',2"-terpyridin]-2-one;

3-chloro-4-((2,4-difluoro-3-methylbenzyl)oxy)-2'-(2-(2-hydroxypropan-2-yl)-5-methylpyrimidin-4-yl)-5",6-dimethyl-2H-[1,4'-bipyridin]-2-one;

3-bromo-4-((2,4-difluoro-3-methylbenzyl)oxy)-2'-(2-(2-hydroxypropan-2-yl)-5-methylpyrimidin-4-yl)-5',6-dimethyl-2H-[1,4'-bipyridin]-2-one; and 3-chloro-4-((2,4-difluoro-3-methylbenzyl)oxy)-6"-(2-hydroxypropan-2-yl)-3",5',6-trimethyl-2H-[1,4':2',2"-terpyridin]-2-one;

3-bromo-4-((2,4-difluoro-3-methylbenzyl)oxy)-6"-(2-hydroxypropan-2-yl)-3",5',6-trimethyl-2H-[1,4':2',2"-terpyridin]-2-one.

4. Compound according to claim 1 of Formula (III):

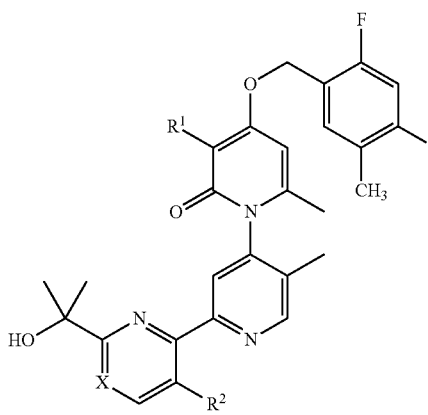

or a pharmaceutically acceptable salt thereof, wherein:
X is CH or N;
$R^1$ is chloro or bromo; and
$R^2$ is —H or methyl.

5. Compound according to claim 4 selected from the group consisting of:
- 3-chloro-4-((2,4-difluoro-5-methylbenzyl)oxy)-2'-(2-(2-hydroxypropan-2-yl)pyrimidin-4-yl)-5',6-dimethyl-2H-[1,4'-bipyridin]-2-one;
- 3-bromo-4-((2,4-difluoro-5-methylbenzyl)oxy)-2'-(2-(2-hydroxypropan-2-yl)pyrimidin-4-yl)-5',6-dimethyl-2H-[1,4'-bipyridin]-2-one;
- 3-chloro-4-((2,4-difluoro-5-methylbenzyl)oxy)-6''-(2-hydroxypropan-2-yl)-5',6-dimethyl-2H-[1,4':2',2''-terpyridin]-2-one;
- 3-bromo-4-((2,4-difluoro-5-methylbenzyl)oxy)-6''-(2-hydroxypropan-2-yl)-5',6-dimethyl-2H-[1,4':2',2''-terpyridin]-2-one;
- 3-chloro-4-((2,4-difluoro-5-methylbenzyl)oxy)-2'-(2-(2-hydroxypropan-2-yl)-5-methylpyrimidin-4-yl)-5',6-dimethyl-2H-[1,4'-bipyridin]-2-one;
- 3-bromo-4-((2,4-difluoro-5-methylbenzyl)oxy)-2'-(2-(2-hydroxypropan-2-yl)-5-methylpyrimidin-4-yl)-5',6-dimethyl-2H-[1,4'-bipyridin]-2-one;
- 3-chloro-4-((2,4-difluoro-5-methylbenzyl)oxy)-6''-(2-hydroxypropan-2-yl)-3'',5',6-trimethyl-2H-[1,4':2',2''-terpyridin]-2-one; and
- 3-bromo-4-((2,4-difluoro-5-methylbenzyl)oxy)-6''-(2-hydroxypropan-2-yl)-3'',5',6-trimethyl-2H-[1,4':2',2''-terpyridin]-2-one.

6. Compound according to claim 1 of Formula (IV):

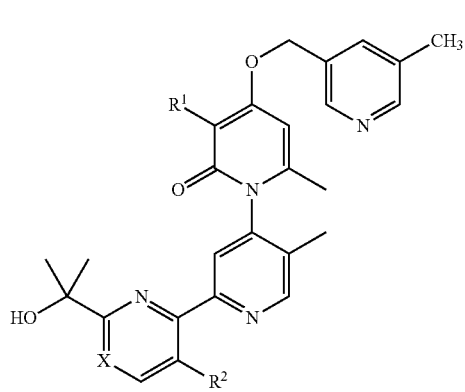

or a pharmaceutically acceptable salt thereof, wherein:
X is CH or N;
$R^1$ is chloro or bromo; and
$R^2$ is —H or methyl.

7. Compound according to claim 6 selected from the group consisting of:
- 3-chloro-2'-(2-(2-hydroxypropan-2-yl)pyrimidin-4-yl)-5',6-dimethyl-4-((5-methylpyridin-3-yl)methoxy)-2H-[1,4'-bipyridin]-2-one;
- 3-bromo-2'-(2-(2-hydroxypropan-2-yl)pyrimidin-4-yl)-5',6-dimethyl-4-((5-methylpyridin-3-yl)methoxy)-2H-[1,4'-bipyridin]-2-one;
- 3-chloro-6''-(2-hydroxypropan-2-yl)-5',6-dimethyl-4-((5-methylpyridin-3-yl)methoxy)-2H-[1,4':2',2''-terpyridin]-2-one;
- 3-bromo-6''-(2-hydroxypropan-2-yl)-5',6-dimethyl-4-((5-methylpyridin-3-yl)methoxy)-2H-[1,4':2',2''-terpyridin]-2-one;
- 3-chloro-2'-(2-(2-hydroxypropan-2-yl)-5-methylpyrimidin-4-yl)-5',6-dimethyl-4-((5-methylpyridin-3-yl)methoxy)-2H-[1,4'-bipyridin]-2-one;
- 3-bromo-2'-(2-(2-hydroxypropan-2-yl)-5-methylpyrimidin-4-yl)-5',6-dimethyl-4-((5-methylpyridin-3-yl)methoxy)-2H-[1,4'-bipyridin]-2-one;
- 3-chloro-6''-(2-hydroxypropan-2-yl)-3'',5',6-trimethyl-4-((5-methylpyridin-3-yl)methoxy)-2H-[1,4':2',2''-terpyridin]-2-one; and
- 3-bromo-6''-(2-hydroxypropan-2-yl)-3'',5',6-trimethyl-4-((5-methylpyridin-3-yl)methoxy)-2H-[1,4':2',2''-terpyridin]-2-one.

8. Compound according to claim 1 of Formula (V):

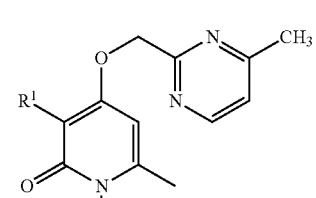

or a pharmaceutically acceptable salt thereof, wherein:
X is CH or N;
$R^1$ is chloro or bromo; and
$R^2$ is —H or methyl.

9. Compound according to claim 8 selected from the group consisting of:
- 3-bromo-2'-(2-(2-hydroxypropan-2-yl)pyrimidin-4-yl)-5',6-dimethyl-4-((4-methylpyrimidin-2-yl)methoxy)-2H-[1,4'-bipyridin]-2-one;

3-chloro-6"-(2-hydroxypropan-2-yl)-5',6-dimethyl-4-((4-methylpyrimidin-2-yl)methoxy)-2H-[1,4':2',2"-terpyridin]-2-one;

3-bromo-6"-(2-hydroxypropan-2-yl)-5',6-dimethyl-4-((4-methylpyrimidin-2-yl)methoxy)-2H-[1,4':2',2"-terpyridin]-2-one;

3-chloro-2'-(2-(2-hydroxypropan-2-yl)-5-methylpyrimidin-4-yl)-5',6-dimethyl-4-((4-methylpyrimidin-2-yl)methoxy)-2H-[1,4'-bipyridin]-2-one;

3-chloro-2'-(2-(2-hydroxypropan-2-yl)pyrimidin-4-yl)-5',6-dimethyl-4-((4-methylpyrimidin-2-yl)methoxy)-2H-[1,4'-bipyridin]-2-one;

3-bromo-2'-(2-(2-hydroxypropan-2-yl)-5-methylpyrimidin-4-yl)-5',6-dimethyl-4-((4-methylpyrimidin-2-yl)methoxy)-2H-[1,4'-bipyridin]-2-one;

3-chloro-6"-(2-hydroxypropan-2-yl)-3",5',6-trimethyl-4-((4-methylpyrimidin-2-yl)methoxy)-2H-[1,4':2',2"-terpyridin]-2-one; and 3-bromo-6"-(2-hydroxypropan-2-yl)-3",5',6-trimethyl-4-((4-methylpyrimidin-2-yl)methoxy)-2H-[1,4':2',2"-terpyridin]-2-one.

10. A pharmaceutical composition comprising a therapeutically effective amount of a compound of claim 1 or a pharmaceutically acceptable salt thereof, and a pharmaceutically acceptable carrier.

11. The pharmaceutical composition of claim 10, further comprising a therapeutically effective amount of an active pharmaceutical ingredient selected from the group consisting of anti-inflammatory drugs, anti-atherosclerotic drugs, immunosuppressive drugs, immunomodulatory drugs, cytostatic drugs, angiogenesis inhibitors, kinase inhibitors, cytokine blockers and inhibitors of cell adhesion molecules.

12. A method for treating lymphoma comprising administering to a subject in need thereof a therapeutically effective amount of a compound of claim 1 or pharmaceutically acceptable salt thereof.

13. The method of claim 12, wherein the subject is a mammal selected from a canine and a humane.

* * * * *